United States Patent
Cerami et al.

[11] Patent Number: 5,850,840
[45] Date of Patent: Dec. 22, 1998

[54] METHODS FOR MEASUREMENT AND TREATMENT PREDICATED ON THE PRESENCE OF ADVANCED GLYCOSYLATION ENDPRODUCTS IN TOBACCO AND ITS COMBUSTION BYPRODUCTS

[75] Inventors: Carla J. Cerami, New York, N.Y.; Richard J. Bucala, Cos Cob, Conn.; Helen Vlassara; Anthony Cerami, both of Shelter Island, N.Y.; Henry W. Founds, Mendham, N.J.

[73] Assignees: Alteon Inc., Ramsey, N.J.; The Picower Institute for Medical Research, Manhasset, N.Y.

[21] Appl. No.: 772,335

[22] Filed: Dec. 23, 1996

Related U.S. Application Data

[60] Provisional application Nos. 60/009,218 Dec. 26, 1995 and 60/009,219 Dec. 26, 1995.

Related U.S. Application Data

[63] Continuation-in-part of Ser. No. 617,350, Mar. 18, 1996, abandoned, and a continuation-in-part of Ser. No. 617,349, Mar. 18, 1996, which is a continuation-in-part of Ser. No. 613,960, Mar. 8, 1996, abandoned, which is a continuation-in-part of Ser. No. 613,234, Mar. 8, 1996.

[51] Int. Cl.$^6$ ........................................................ A24F 1/10
[52] U.S. Cl. ............................................. 131/330; 131/270
[58] Field of Search ..................................... 131/270, 330, 131/331; 436/86, 901

[56] References Cited

U.S. PATENT DOCUMENTS

| | | |
|---|---|---|
| 2,258,321 | 10/1941 | Ericks . |
| 2,289,541 | 7/1942 | Bricks et al. . |
| 2,300,570 | 11/1942 | Heuser et al. . |
| 2,375,659 | 5/1945 | Jones et al. . |

(List continued on next page.)

FOREIGN PATENT DOCUMENTS

| | | |
|---|---|---|
| 134099 | 11/1969 | Czechoslovakia . |
| 111211 | 6/1984 | European Pat. Off. . |
| 0 158 020 | 10/1985 | European Pat. Off. . |

(List continued on next page.)

OTHER PUBLICATIONS

Acharya et al. 1988. *Biochemistry* 27(12): 4522–9.
Baylin et al. (1975) Experimentia 31:562–64.
Beaven et al. (1969) J. Pharm. Exp. Ther. 165:14–22.

(List continued on next page.)

*Primary Examiner*—David H. Willse
*Assistant Examiner*—Kelly O'Hara
*Attorney, Agent, or Firm*—Klauber & Jackson

[57] ABSTRACT

Methods are provided for measuring the accumulation of advanced glycosylation endproducts (AGEs), and for lowering the accumulation of advanced glycosylation endproducts, which are predicated on the discovery that such AGEs and their precedent glycotoxins are present in tobacco and its byproducts. More particularly, the methods focus on the observation that individuals who smoke or otherwise use tobacco have increased levels of AGEs relative to non-smoking individuals. The present methods relate to the measurement of AGE levels in both individuals and in tobacco and its byproduct, smoke, and to the treatment of such individuals with agents capable of reacting with glycosylation products to either avert or diminish the accretion of AGEs in the body. Methods are also provided for the evaluation of the tobacco products to determine their storage status and organoleptic capacity and potential, for the treatment of the ambient atmosphere to lower AGE levels, and for the treatment of the tobacco products and combustion byproducts to lower AGE levels therein. For example, air or other samples may be taken and evaluated by a dosimeter or like device, to determine whether AGE levels exceed normal, after which measures could be implemented to remediate the ambient condition. Likewise, filters and similar devices for removing AGEs from tobacco smoke are provided. All such methods and corresponding materials are contemplated and included.

4 Claims, 11 Drawing Sheets

U.S. PATENT DOCUMENTS

| | | |
|---|---|---|
| 2,721,217 | 10/1955 | Peters et al. . |
| 2,928,829 | 3/1960 | Mull . |
| 2,951,843 | 9/1960 | Haack et al. . |
| 3,006,913 | 10/1961 | Mull . |
| 3,053,732 | 9/1962 | Greenhalgh . |
| 3,055,882 | 9/1962 | Mull . |
| 3,055,883 | 9/1962 | Mull . |
| 3,081,222 | 3/1963 | Hagemann et al. . |
| 3,098,066 | 7/1963 | Mull . |
| 3,101,336 | 8/1963 | James et al. . |
| 3,178,433 | 4/1965 | Mull . |
| 3,183,241 | 5/1965 | Oja . |
| 3,200,111 | 8/1965 | Paquette . |
| 3,201,459 | 8/1965 | Coda et al. . |
| 3,202,710 | 8/1965 | Bolger . |
| 3,283,003 | 11/1966 | Jack et al. . |
| 3,291,829 | 12/1966 | Mull . |
| 3,317,545 | 5/1967 | Albrecht et al. . |
| 3,320,195 | 5/1967 | Braun . |
| 3,364,220 | 1/1968 | Biel et al. . |
| 3,506,680 | 4/1970 | Berger et al. . |
| 3,637,850 | 1/1972 | Houlihau et al. . |
| 3,681,504 | 8/1972 | Johnston et al. . |
| 3,746,764 | 7/1973 | Nordmann et al. . |
| 3,803,324 | 4/1974 | Winter et al. . |
| 3,978,060 | 8/1976 | Forsythe et al. . |
| 3,980,774 | 9/1976 | Hegarty et al. . |
| 3,991,209 | 11/1976 | Forsythe et al. . |
| 4,161,541 | 7/1979 | Rasmussen . |
| 4,271,190 | 6/1981 | Bertelmann et al. . |
| 4,471,137 | 9/1984 | Barton et al. . |
| 4,544,759 | 10/1985 | Hlavaka et al. . |
| 4,665,192 | 5/1987 | Cerami et al. . |
| 4,680,300 | 7/1987 | Nelson et al. . |
| 4,731,383 | 3/1988 | Erczi et al. . |
| 4,758,583 | 7/1988 | Cerami et al. . |
| 4,908,446 | 3/1990 | Ulrich et al. . |
| 4,978,684 | 12/1990 | Cerami et al. . |
| 4,983,604 | 1/1991 | Ulrich et al. . |
| 5,006,523 | 4/1991 | Atwal . |
| 5,017,696 | 5/1991 | Farmar et al. . |
| 5,140,048 | 8/1992 | Ulrich et al. . |
| 5,189,046 | 2/1993 | Burch et al. . |
| 5,196,450 | 3/1993 | Sjoerdsma et al. . |
| 5,296,498 | 3/1994 | Malen et al. . |
| 5,336,689 | 8/1994 | Weber et al. . |

FOREIGN PATENT DOCUMENTS

| | | |
|---|---|---|
| 0 222 313 | 11/1986 | European Pat. Off. . |
| 325936 | 1/1989 | European Pat. Off. . |
| 316852 | 5/1989 | European Pat. Off. . |
| 327919 | 8/1989 | European Pat. Off. . |
| 372603 | 6/1990 | European Pat. Off. . |
| 2059975 | 6/1971 | France . |
| 2029707 | 12/1970 | Germany . |
| 3040993 | 6/1982 | Germany . |
| 45-27114 | 9/1970 | Japan . |
| 54-138136 | 10/1979 | Japan . |
| 60-27371 | 2/1985 | Japan . |
| 60-118174 | 6/1985 | Japan . |
| 62-142114 | 6/1987 | Japan . |
| 64-56614 | 8/1987 | Japan . |
| 63-287492 | 11/1988 | Japan . |
| 809165 | 5/1957 | United Kingdom . |
| 952194 | 12/1961 | United Kingdom . |
| 1274668 | 6/1968 | United Kingdom . |
| 1036987 | 7/1968 | United Kingdom . |
| 1458636 | 9/1974 | United Kingdom . |
| WO 92/07560 | 5/1992 | WIPO . |

OTHER PUBLICATIONS

Brown et al. Abst., Assoc. for Minority Phys., Oct. 27, 1989, Washington DC.
Brown et al. (1990) J. Am. Soc. Nephrology, vol. I, No. 4, p. 329.
Brownlee CA 111:70141f.
Brownlee et al. CA 105:72441d.
Brownlee et al. (1985) Diabetes 34:938–40.
Brownlee et al. (1986) Diabetes 35 (Suppl. 1):42 A.
Brownlee et al. 1986. Science 232: 16929–32.
Brownlee et al. 1984. Ann. Int. Med. 101: 527–37.
Brownlee et al. 1983. J. Exp. Med. 158: 1739–44.
Bucala et al, 1984, PNAS 1984, 81: 105–109.
Bucala 1985, PNAS 82:8439–8442.
Bunn et al. 1975. Biochem. Biophys. Res. Comm. 67: 109–9.
Cameron et al. (1992) Diatetologia 35:946–50.
Carroll et al. (1984) Fed. Proc. 43:Abst.2514.
Dabrowski et al. (1983) Acta. Physiol. Pol. 34:91–7.
Dabrowski et al. (1984) Agents and Actions 14:458–60.
Ebetino et al. 1962. J. Org. Chem. 27: 188–91.
Ebetino et al. 1964. J. Org. Chem. 29: 2582–5.
Eble et al. (1983) J. Biol. Chem. 258:9406–12; CA99:219(84008p).
Finot. 1982. in Food and Nutritional Aspects. Feeney and Whitaker, eds. American Chemical Society 198: 91–124.
Flier et al. (1988) New Eng. J. Med. 318: 1315–21.
Fong et al. (1989) diabetes 38:84A.
Geisen, K. (1987) Abst., 22nd Annual Meeting of the German Diabetes Association (translated by P. Ulrich).
Giambrone et al. (1989) Diabetes 38, Suppl.2:83A.
Godfrey. 1962. Doctoral Dissertation. U. of London.
Harding, J.J. (1985) Adv. Prot. Chem. 37:247–66.
Hayase et al., J. Biol. Chem., 263:3758–3764 (1989).
Hollis et al. (1984) Exp. Mol. Path. 41:207–17.
Hollis et al. (1985) Diabetologia 28:282–5.
Hollis et al. (1984) Fed. Proc. 43:Abst.2513.
Hollis et al. (1985) Exp. Mol. Path. 43:90–6.
Khatami et al.CA 110:643b.
Kihara et al. (1991) Proc. Natl. Acad. Sci. USA 88:6107–11.
Kohn et al. 1984. Diabetes 33(1): 57–9.
Koenig et al. 1977. J. Biol. Chem. 252: 2992–7.
Kumari et al. (1991) Diabetes 40:107985.
Lee AT and Cerami, A. 1987, PNAS 84:8311–8314.
Lee et al. (1994) FASEB Journal 8:545–550.
Levine et al. (1969) Ann. New York Acad. Sci., pp. 246–256.
Levine et al. (1966) Biochem. Pharmacol. 15:841–9.
Lewis et al. (1990) Exp. Eye Res. 50:463–7.
Lewis et al. CA 113:34670k.
Lindberg et al. (1966) Acta. Obst. Gyn. (Scandianav) 45:131–9.
Maillard. C.R. Acad. Sci. 154: 66–8.
Merk Index (1983) 10th ed., p. 66: #444.
Merk Index (1989) 11th ed., #453: Aminoguanidine.
Merk Index (1976) 9th ed., p. 60: #447.
Merk Index, 16th ed., p. 691: #2476.
Monnier et al. 1984. Proc. Natl. Acad. Sci. 81: 583–7.
Monnier and Cerami. 1983. in Maillard Reaction in Food and Nutrition. Waller, ed. American Chemical Society 215: 431–49.
Monnier and Cerami. 1983. Biochem. Biophys. Acta. 760: 97–103.
Monnier and Cerami. 1982. Clin. Endocrinol. Metab. 11: 431–52.
Monnier and Cerami. 1981. Science 211: 491–3.

Murdock et al. 1982. J. Med. Chem. 25: 505–18.
Nicholls et al. (1989) Lab. Invest. 60:486–91.
Nicholls et al. CA 111:37368.
Odetti et al. (1990) Diabetes 39:796–801.
Oimomi et al. (1989) Agric. Biol. Chem. 53:1727–8.
Oimomi et al. CA 111: 70766p.
Onada et al. CA 112:42594h.
Orlidge et al. (1982) Arteriosclerosis 2:142–50.
Owens et al. (19821) Arteriosclerosis 1:265–72.
Oxlund et al., Abst., Prog. for the Symp. Glycated Prot. in Diabetes Mellitus, Adelaide, South Australia, Nov. 16–Aug. 1988.
Oxund et al., Abst. #371.
Oxlund et al. (1992) Diabetologia 35:19–25.
Ponger et al. 1984. *Proc. Natl. Acad. Sci.* USA 81: 2684–8.
Potekhin et al. 1973. Zhurnal Organicheskoi Khimii 9:1180–6.

Sell, D. and Monnier V., J. Biol. Chem., 264:21597–21602 (1989).
Soulis et al., Abst., NIH Conf. Maillard Reaction in Aging, Diabetes, Nutrition, Bethesda, Maryland, Sep. 1922–Mar. 1988.
Soulis et al., Abst. Prog. for the Symp. Glycated Prot. in Diabetes Mellitus, Adelaide, South Australia, Nov. 16–Aug. 1988.
Soulis–Liparot et al. (1991) Diabetes 40:1328–34.
Stoner et al. 1985. *Agents and Actions* 17:5–9.
Sundberg et al. 1990. *J. Med. Chem.* 33: 298–307.
Tai et al. 1984. *J. Med. Chem.* 27:236–8.
Vlassara et al. (1992) Proc. Natl. Acad. Sci. USA 89:12043–7.
Yamashita et al. (1989) Diabetes 38:25A.

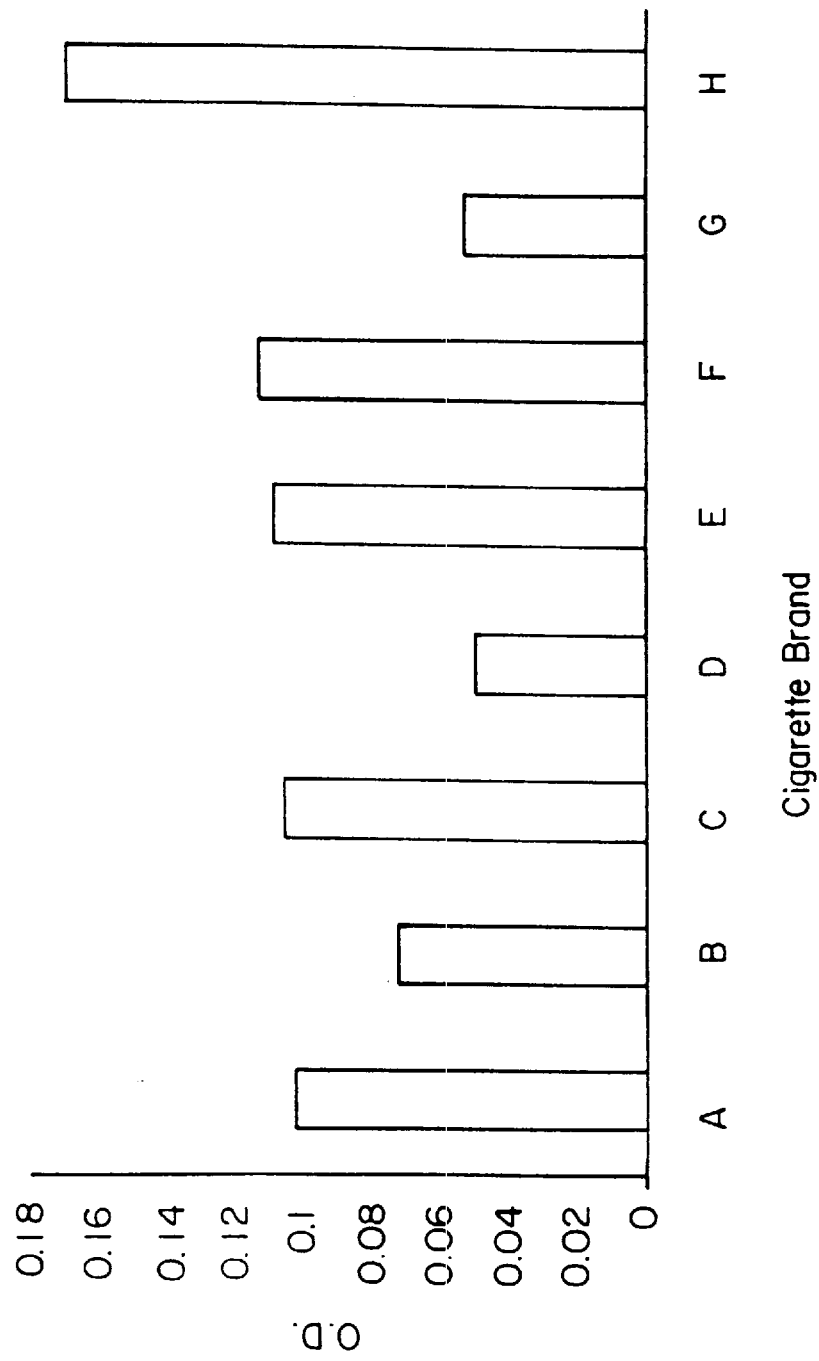

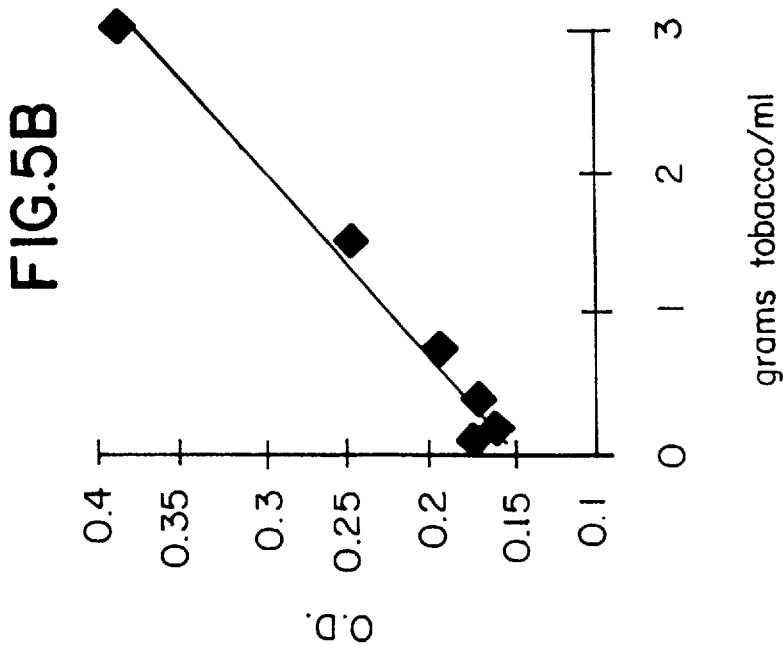

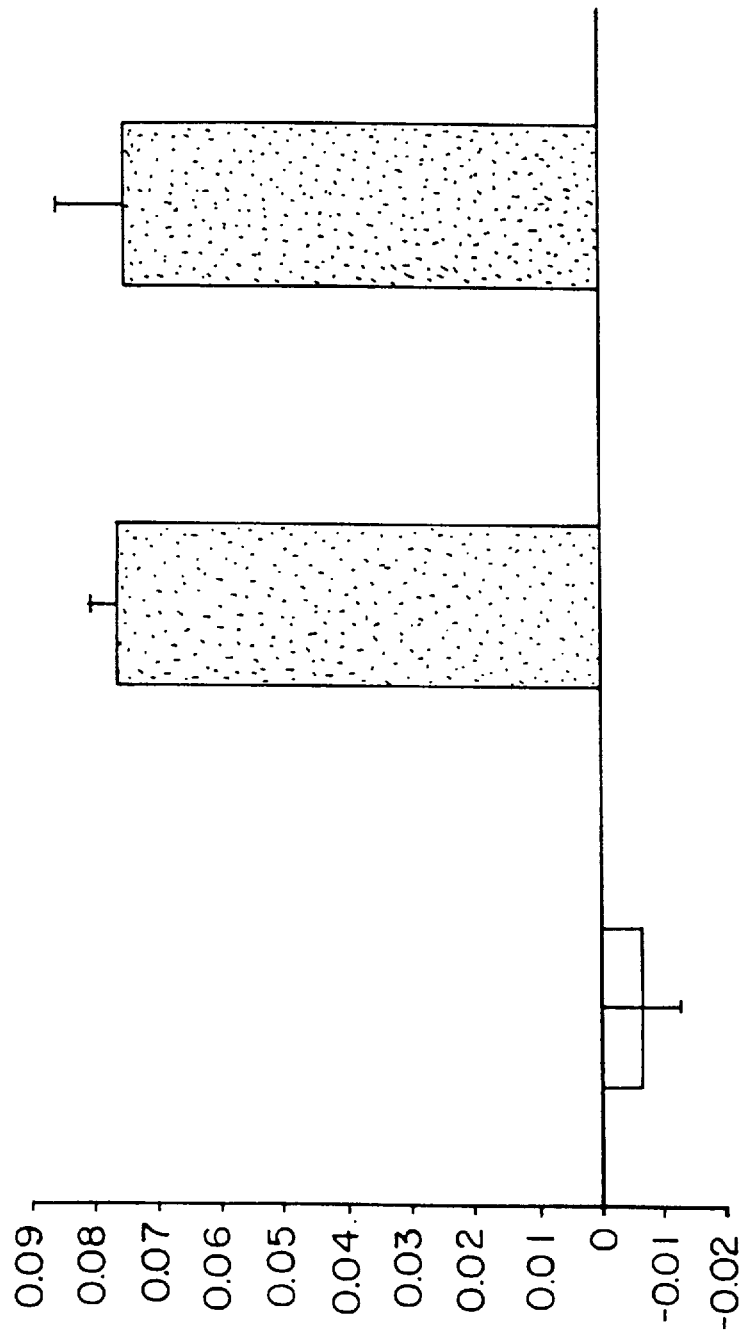

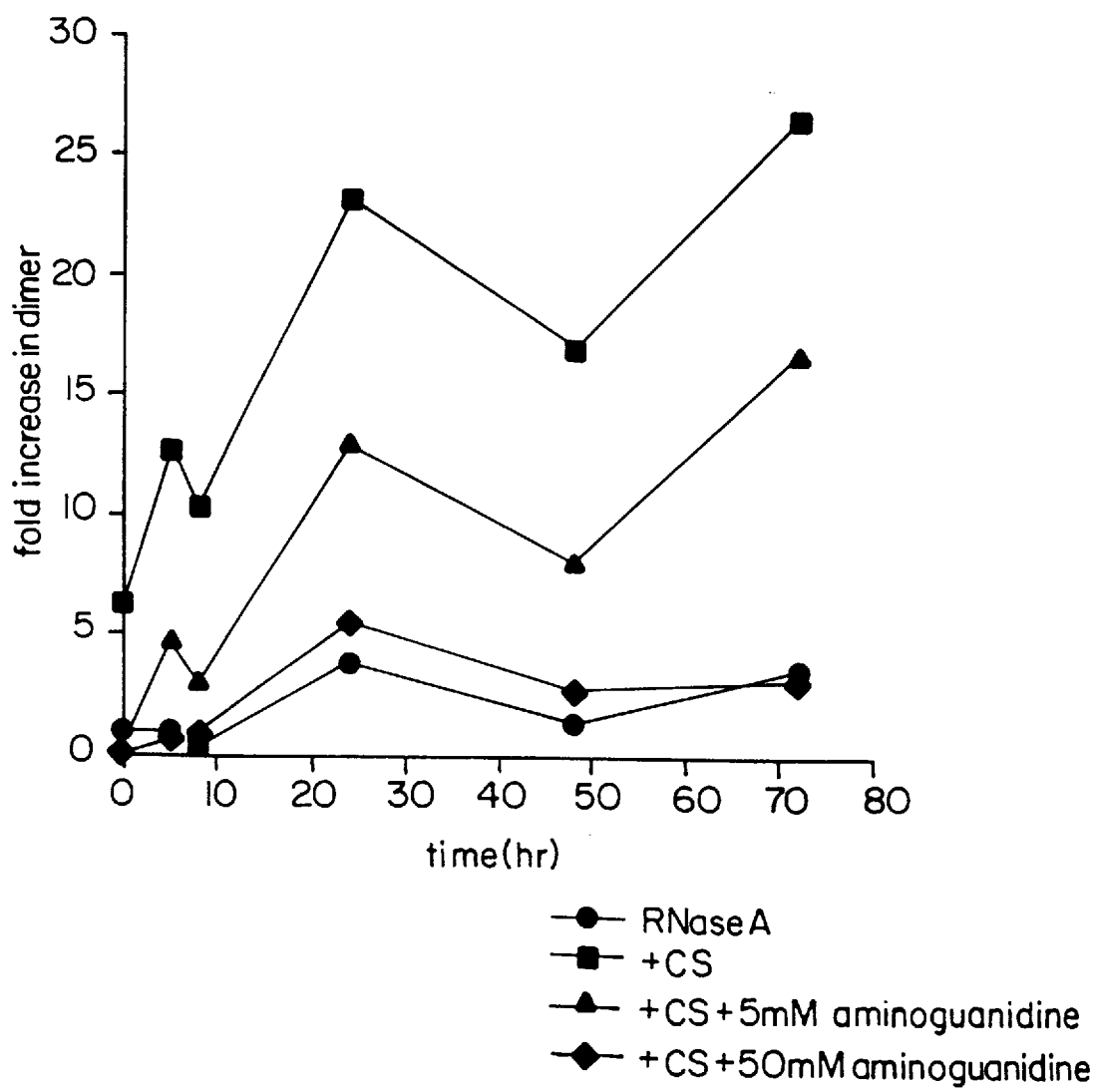

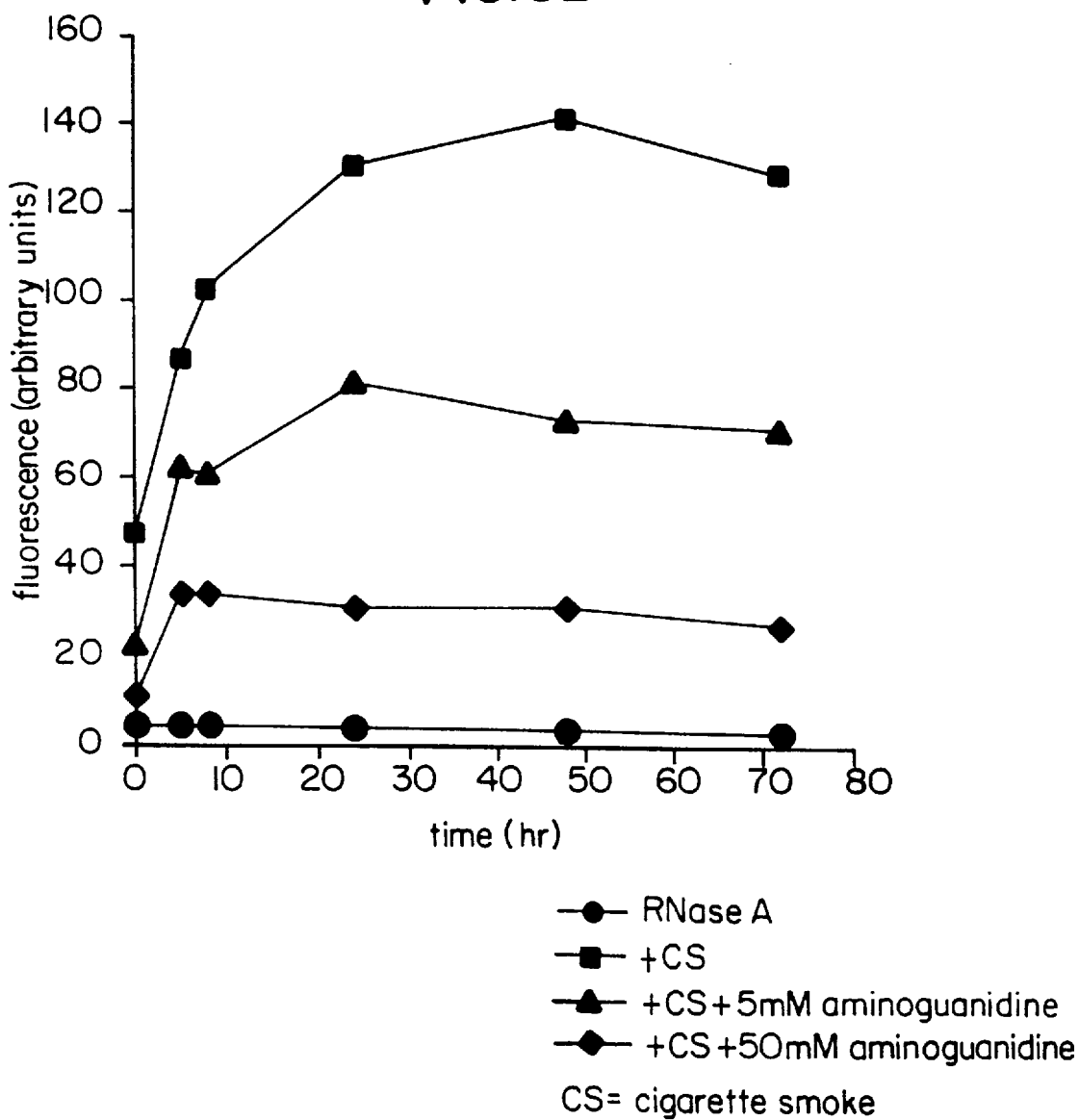

METHODS FOR MEASUREMENT AND TREATMENT PREDICATED ON THE PRESENCE OF ADVANCED GLYCOSYLATION ENDPRODUCTS IN TOBACCO AND ITS COMBUSTION BYPRODUCTS

CROSS REFERENCE TO RELATED APPLICATIONS

The present application is a Continuation In Part of application Ser. Nos. 08/617,350, now abandoned, and 08/617,349, pending, both filed Mar. 18, 1996, which are in turn, Continuation In Part applications based on respective application Ser. Nos. 08/613,960, abandoned, and 08/613,234, pending, both filed Mar. 8, 1996, which are in turn, based on respective U.S. Provisional application Ser. Nos. 60/009,218 and 60/009,219, both filed Dec. 26, 1995, and now abandoned. Applicants claim the benefit of all of the above applications under 35 U.S.C. §120.

TECHNICAL FIELD OF THE INVENTION

The present invention relates generally to the correlation between the use of tobacco products such as cigarettes, and the presence of advanced glycosylation endproducts (AGEs), and to the diagnostic, therapeutic and industrial applications to which this observation and relationship may be beneficially directed. More particularly, the invention directs itself to the observation that the consumption of tobacco products increases the amount of AGEs in vivo, with concomitant increases in risk and incidence of maladies associated with both smoking and AGE accumulation, and to the detection of AGEs in tobacco, tobacco smoke and extracts thereof, as well as in tobacco users, both to detect undesirable excesses in AGE levels and to evaluate tobacco and smoking materials on a commercial scale. The invention also extends to the use of inhibitors of the formation of AGEs in a variety of contexts to treat or prevent undesirable excesses in AGE levels, as well as to modify tobacco and smoking materials on a commercial scale.

BACKGROUND OF THE INVENTION

The deleterious effects of tobacco smoking on human health have been extensively documented. Among other things, such conditions as cancer and coronary artery disease are dramatically elevated in incidence and severity in the case of smokers, and such patients likewise present significant alterations in lipoprotein profiles and increases in oxidized LDLs. Increased occurrence and severity of coronary artery disease and dyslipidemia, among other things, have also been observed in patients having elevated levels of advanced glycosylation endproducts (AGEs), and the coincidence of these observations set the stage for the discovery that underlies the present invention.

The nonenzymatic reactions between glucose and proteins has been recognized for many years, but molecular details of these reactions, and the biological and medical consequences of nonenzymatic glycation in vivo, are still emerging today. The earliest recognized manifestation of nonenzymatic glycation was in the appearance of brown pigments during the cooking of food, which was identified by Maillard in 1912, and lent the term "browning" to this branch of food chemistry. Maillard observed that glucose or other reducing sugars react spontaneously with amino-containing compounds such as amino acids and peptides to form initial Schiff base adducts. This condensation product then undergoes a series of additional spontaneous dehydrations, rearrangements and other reactions to form the class of brown pigments, now known as advanced glycosylation endproducts, or AGEs.

In the years that followed its initial discovery, food chemists studied the Maillard reaction in detail and determined that stored and heat-treated foods undergo nonenzymatic browning as a development of the initial reaction between glucose and the polypeptide chain, and that the proteins are resultingly crosslinked and correspondingly exhibit decreased bioavailability. At this point, it was determined that the pigments responsible for the development of the brown color in protein glycosylation (or advanced glycation) also possess characteristic absorptive spectra and fluorescent properties.

The reaction between reducing sugars and food constituents discussed above was found in recent years to have its parallel in vivo. Thus, the nonenzymatic rearrangement of the initial Schiff base formed by addition of glucose to a free amino group on a protein forms the stable amino, 1-deoxy ketosyl adduct known as the Amadori product. (A parallel reaction involving a reducing ketose rather than an aldose generates an early glycation product known as the Heyns rearrangement product). Accumulation of this early glycation adduct has been shown to occur with hemoglobin, wherein a rearrangement of the amino terminus of the β-chain of hemoglobin following an initial reaction with glucose forms the modified hemoglobin known as hemoglobin $A_{1c}$, a clinically important marker of glucose control in diabetes. Glycation reactions have also been found to occur with a variety of other body proteins, such as lens crystallins, collagen nerve proteins, and low density lipoproteins, as well as DNA and aminophospholipids.

The Maillard browning process generates a widely diverse array of advanced glycosylation products, each of which occurs in very low yield. This diversity has made identification and structural determination of specific AGEs a difficult proposition. In U.S. Pat. No. 4,665,192 the fluorescent chromophore 2-(2-furoyl)-4(5)-2(furanyl)-1H-imidazole was isolated and identified from certain browned polypeptides such as bovine serum albumin and poly-L-lysine. This success encouraged the subsequent identification of additional advanced glycosylation endproducts and assisted additional investigations seeking to clarify the chemistry of the protein aging process and to identify the specific reactants, intermediates and products involved in order to develop methods and agents for inhibiting glycation.

More recently, other advanced glycosylation products have been identified, such as AFGP (Farmar et al., U.S. Pat. No. 5,017,696, issued May 21, 1991); pyrraline (Hayase et al., "Aging of Proteins: Immunological Detection of a Glucose-derived Pyrrole Formed during Maillard Reaction in vivo", *J. Biol. Chem.*, 263: 3758–3764 (1989)), and pentosidine (Sell, D. and Monnier V. "Structure Elucidation of a Senescence Cross-link from Human Extracellular Matrix", *J. Biol. Chem.*, 264: 21597–21602 (1989)).

A large body of evidence has been assembled to show that Maillard products as a whole underlie a wide variety of both normal and pathogenic activities and responses that occur as AGEs accumulate in vivo. Such activities may be direct, as a consequence of the chemical reactivity of glycation products and adducts; or indirect, mediated by the cellular recognition of glycation adducts and products via AGE-specific binding proteins or receptors.

Although most studies describing the pathogenic role of AGE accumulation in vivo have focused on AGE-proteins and AGE-peptides, the reaction between the lipids, and particularly, low-density lipoprotein (LDL) and glucose to form lipid-AGEs also has been determined to play a pathogenic role, for instance, in atherogenesis, where the formation of foam cells marks the accumulation of atherosclerotic plaques. Oxidation and glycation of the protein and lipid components of low-density lipoprotein (LDL) results in the loss of the recognition of the apo B component by cellular LDL receptors, prolonging the circulating half-life of this LDL and resulting in the preferential uptake of oxidized-LDL (ox-LDL) or otherwise modified LDL via macrophage "scavenger" receptors, AGE receptors, and other specialized cellular mechanisms. The enhanced endocytosis of ox-LDL by vascular wall macrophages has been linked to their transformation into lipid-laden foam cells that characterize early atherosclerotic lesions. Previous studies also have shown that AGE modification of LDLs increases the potential for lipid oxidation.

The "family" of AGEs includes relatively stable species which can be isolated and characterized by chemical structure, while others are unstable or reactive and their structural determination has therefore been problematic. Labile or reactive AGEs can be "trapped" by specific chemical agents, and such reactions and trapping have been used not only to gain structural insights but also to inhibit the glycation process for therapeutic purposes. AGE-lipids may also be stable, unstable or reactive.

An appreciation for the pathogenic potential of AGEs has suggested that interference with, or inhibition of, advanced glycation chemistry could be of enormous therapeutic benefit. In this connection, a series of agents has been discovered, as exemplified by aminoguanidine (also known as Pimagedine), that are useful glycation inhibitors. This compound, and others like it, have been theorized to react with the carbonyl moiety of the early glycosylation product of a target protein (or other biomolecule) formed subsequent to the initial nonenzymatic reaction with glucose or another reducing sugar, and thereby prevent further reaction to form advanced glycosylation endproducts.

A variety of other inhibitors of advanced glycation reactions are also known, many of which are thought to be particularly effective at stages of the Maillard reaction other than those which are most susceptible to inhibition by aminoguanidine and its analogs. For instance, certain compounds, or compositions thereof, having an active aldehyde substituent, such as acetaldehyde, are effective inhibitors of the advanced glycation pathway. This activity is thought to arise by the reaction of such active aldehyde agents with the glycosyl-amino moieties of glycation products formed in the initial stages of the Maillard reaction, i.e., these agents react with the Amadori and Heyns rearrangement products, which are early glycation products. Other agents that may serve in a similar capacity, are those that include a conserved binding motif which comprises a common 17–18 amino acid cysteine-bounded hydrophilic peptide loop domain, initially discovered and identified in the antibacterial proteins lysozyme and lactoferrin. More particularly, exemplary agents include molecules having an hydrophilic loop domain, which hydrophilic loop domain has a structure corresponding to $R_1Z_1Xaa_nZ_2R_2$ (SEQ ID NOS:1–6), wherein $Z_1$ and $Z_2$ are residues capable of forming a cross-link; $R_1$ and $R_2$ are independently a polypeptide, a $C_1$ to $C_{12}$ alkyl, aryl, heteroalkyl, or heteroaryl group, or hydrogen; Xaa is any L- or D-amino acid; and n=13–18. Such agents and their uses are set forth in International Publication No. WO 96/31537, published Oct. 10, 1996 incorporated herein by reference. Yet other agents such as certain thiazolium compounds, are particularly effective at preventing advanced glycation, and even reversing the formation of advanced glycation endproducts and associated cross-linking moieties through reactions with late glycation products.

The compounds, and their compositions, utilized in this invention are thought to react with early glycosylation products, thereby preventing the same from later forming the advanced glycosylation end products which lead to cross-links, and thereby, to molecular or protein aging and other adverse molecular consequences. All of such various glycation pathway inhibitors and other compounds reactive with early and late glycation products, either alone or in combination, find use in ameliorating the pathogenic potential of AGEs that accumulate in the body.

AGEs may accumulate through de novo formation in vivo, through reattachment of AGEs liberated in vivo by cellular activities, or as revealed herein by Applicants, by exposure to exogenous AGEs, for instance by smoking. Accordingly, the significance of the reactive pathways of AGEs and their observed presence in tobacco and tobacco smoke lends further importance and encouragement to the need for the development of effective techniques for monitoring the smoking habits of individuals, as well as the development of effective agents and devices to reduce the transfer of AGEs by tobacco use. Such monitoring techniques would be useful for gathering the history of such smokers, and also for monitoring their medical condition and particularly, their predisposition to the conditions that are associated with elevated levels of AGEs. Measurement of AGEs in tobacco would facilitate the evaluation of tobacco crops, as well as providing an index of the amount of AGEs that would be transferred to a smoker during the consumption of smoking materials prepared from the crops in question; in this regard, AGEs may also be evaluated in tobacco smoke. Effective therapeutic strategies, methods and agents in this regard may address the inhibition of AGEs in tobacco, in smoking materials, and would include the development of filter devices and like materials for use in conjunction with tobacco smoking, or in the protection or treatment of individuals of the smoking or smoke-exposed populations. It is toward the fulfillment of all of the above recited objectives that the present invention is directed.

SUMMARY OF THE INVENTION

The present invention derives from the discovery that tobacco and its combustion byproducts such as smoke, contain advanced glycosylation endproducts (AGEs) which are, as a group, reactive with amine-containing biomolecules, especially proteins, and that consequently, individuals who smoke or otherwise use tobacco generally exhibit increases in AGE levels throughout the blood and tissues. The elevation in such levels has been linked to the increased incidence of the pathologies, such as increased risk for coronary disease, atherosclerosis and other maladies, associated with enhanced accumulation of AGEs.

Accordingly, the invention recognizes the presence of AGEs in tobacco, tobacco products for use as by smoking, and the combustion byproducts of tobacco and in biological samples taken from smokers. In a first aspect, the invention extends to the measurement of AGEs in tobacco smoking materials, in the combustion byproducts of tobacco, and in biological samples taken from smokers, to identify AGE levels and to thereby facilitate an estimate of the likelihood or history of exposure of an individual to such AGEs during smoking, or to provide information on the condition of the tobacco or tobacco products including, for example, to evaluate the age, flavor and/or storage status (freshness) of a tobacco crop.

More particularly, the measurement and evaluation of smokers would serve both to apprise the healthcare professional and the patient of any pathological conditions that may either have a high likelihood of onset, or that, if present, bear close periodic monitoring and/or indicate the need for therapeutic intervention, and to assess the extent and consequent risk that the smoker assumes from the smoking habit. The latter consideration would attend the evaluation of the patient as participant in a program for the purpose of stopping smoking, as well as to assess the extent of the test subject's smoking history, for insurance or like investigative purposes to confirm the cessation of tobacco use (or lack thereof).

The measurement of AGEs may be made by treating a sample of tobacco to form an extract in which AGEs are suspected to be present, followed by the analysis of the extract for such purpose. In one embodiment, the sample may be treated by combustion to form smoke, and the smoke is then examined for the presence and amount of AGEs. Alternately, the extract may proceed from a chemical treatment of the tobacco alone. One may also examine the body fluids and tissues of the smoker to determine the level and extent of AGEs present as a result of smoking. The results would be compared to a standard developed from non-smoking individuals otherwise sharing the same medical profile as the patient under test.

The invention includes the preparation of agents to specifically recognize tobacco-relate AGEs, such as antibodies that are specifically directed against the AGEs found in tobacco and tobacco smoke, to facilitate the detection of tobacco-related AGEs and the evaluation of the medical status of tobacco smokers. Such agents would be incorporated into test kits and the like for use in the performance of such evaluations.

In a related aspect, dosimeters may be prepared with a substrate or carrier retaining and bearing a glycation target molecule, such as an amine-bearing moiety, fixedly associated therewith, and capable of reacting with AGEs present in a sample, be it a sample of ambient air or a biological sample taken from a patient. The dosimeter may be used in conjunction with the diagnostic protocols and test kits set forth herein.

The invention further extends to methods for detecting and measuring the levels of advanced glycosylation endproducts in individuals who smoke tobacco, by gathering a biological sample from such individuals and thereafter examining the sample for the presence and amount of advanced glycosylation endproducts. The sample gathered may extend to cells, tissue, serum, saliva, urine or feces, and the techniques for detection and measurement have been developed and utilized with respect to AGEs in the past.

In a further aspect, the invention extends to the preparation of antagonists such as antibodies, binding motifs and chemical inhibitors of advanced glycation that are specifically directed against the AGEs found in tobacco and tobacco smoke.

The present invention also extends to a method and associated agents for use in the treatment of conditions in individuals who are tobacco users or smokers, which comprise such methods and agents as are useful for the inhibition of protein aging and particularly, such agents as are capable of reacting with glycosylation products to counteract their formation and/or the deleterious activity of such AGEs.

In particular, agents for inhibiting protein aging due to the formation of advanced glycosylation endproducts may be selected from the group consisting of aminoguanidine, agonists, analogs, congeners, cognates and mimics thereof; and mixtures thereof.

Such agents may also include and may be selected from materials capable of reacting with the glycosyl-amino moiety of the early glycosylation product (also known as the Amadori and Heyns products) formed by the reaction of glucose, or other reactive sugars, with a biomolecule presenting a glycation-susceptible moiety, such as an amino group on a protein, thus stabilizing this early glycosylation product, and preventing its further reaction to form advanced glycosylation end products. Thus, for example, compounds or compositions having an active aldehyde substituent, and more particularly, compounds such as acetaldehyde are suitable. This activity is thought to arise by the reaction of such active aldehyde agents with the glycosyl-amino moieties of glycation products formed in the initial stages of the Maillard reaction, i.e., these agents react with the Amadori and Heyns rearrangement products, which are early glycation products.

More particularly, these agents may comprise compounds that participate in the formation of products having either formula I or II

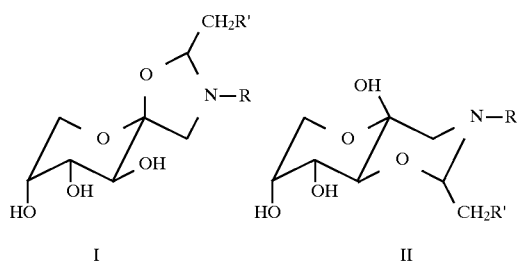

wherein R is the residue of an amino-containing peptide or protein, prepared by reacting the glycosyl-amino moiety of the early glycosylation product (also known as the Amadori or Heyns product) formed by the reaction of glucose, or other reactive sugars, with a protein, with an agent containing a reactive aldehyde group. Typical agents of this class are described in Provisional application Ser. No. 60/006,752, for "Improved Method and Agent for Inhibiting Protein Aging," filed Nov. 15, 1995, which is incorporated herein by reference.

Other agents, such as certain thiazolium compounds, are particularly effective at preventing advanced glycation, and even reversing the formation of advanced glycation endproducts and associated cross-linking moieties, through reactions with late glycation products. Exemplary compounds and compositions that are effective against pre-existing or late glycation adducts are thought to operate by reacting with, and causing the cleavage of, α-dicarbonyl segments within existing AGEs, particularly as such α-dicarbonyl segments occur within AGE structures that form inter- or intra-molecular cross-links. The thiazolium-based compounds preferably operate in this regard in a catalytic fashion which regenerates the original, active thiazolium derivative that may then catalyze the cleavage of additional existing AGE moieties. Typical agents of this class may comprise thiazolium compounds having the following structural formula:

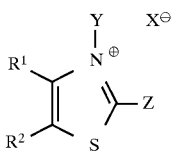 (III)

wherein $R^1$ and $R^2$ are independently selected from the group consisting of hydrogen, hydroxy(lower)alkyl, acetoxy (lower)alkyl, lower alkyl, lower alkenyl, or $R^1$ and $R^2$ together with their ring carbons may be an aromatic fused ring, optionally substituted by one or more amino, halo or alkylenedioxy groups;

Z is hydrogen or an amino group;

Y is amino, a group of the formula

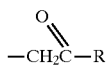

wherein

R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups;

a group of the formula

wherein

R' is hydrogen, or a lower alkyl, lower alkynyl, or aryl group;

or a group of the formula

wherein

R" is hydrogen and R'" is a lower alkyl group, optionally substituted by an aryl group, or an aryl group, said aryl group optionally substituted by one or more lower alky, halo, or alkoxylcarbonyl groups; or R" and R'" are both lower alkyl groups;

X is a halide, tosylate, methanesulfonate or mesitylenesulfonate ion;

and mixtures thereof.

The compounds, and their compositions, utilized in this invention are thought to react with early glycosylation products, thereby preventing the same from later forming the advanced glycosylation end products which lead to cross-links, and thereby, to molecular or protein aging and other adverse molecular consequences. Additionally, said compounds and compositions are thought to react with already formed advanced glycosylation end products to reduce the amount of such products. These agents are described in greater detail in application Ser. No. 08/375,155, which is incorporated herein by reference.

The present invention further extends to methods for the reduction of the accumulation of advanced glycosylation endproducts particularly in individuals who are tobacco smokers or otherwise consume tobacco products, by treating such individuals with agents that are known to inhibit the formation of advanced glycosylation endproducts, such as those agents set forth above herein. Said agents find particular utility in the several diseases and pathological conditions the incidence or severity of which has been associated with tobacco consumption, especially by cigarette smoking, such as cardiovascular, cerebrovascular and peripheral vascular diseases including, for instance, heart and coronary artery disease, arrhythmia, atherosclerosis, stroke, hypertension, pulmonary infection, thromboangiitis obliterans, peripheral occlusive vascular disease, Raynaud's disease, claudication and renal failure; pulmonary and lung diseases such as chronic obstructive pulmonary disease, chronic bronchitis, emphysema, asthma, and eosinophilic granuloma of the lung; various cancers including, without limitation, lung cancer, cancer of the mouth, head and neck, mesothelioma, esophageal, bladder, cervical, endometrial, pancreatic and renal cell cancer; peptic, gastric and esophageal ulcer; hyperlipidemia and dyslipidemia; osteoporosis; scleroderma, snuff keratosis and oral leukoplakia; immune suppression; and staining of teeth and skin.

In addition to the direct treatment of the individuals, the present method extends to the treatment of the tobacco materials themselves to reduce the generation as well as the passage of such AGEs to the consumer or bystander. In a first instance, therefore, the method would comprise the treatment of the tobacco materials themselves by chemical means or otherwise, to reduce the formation or presence of advanced glycosylation endproducts. As certain tobaccos are cured with sugar, such method could extend to the treatment of the cured tobacco so that a reduction in the content of AGEs or their precedent glycotoxins as defined herein, is accomplished.

A further embodiment of the treatment of the tobacco materials would comprise the preparation of an appropriate filter medium for use in conjunction with the tobacco endproduct or cigarette, which filter medium would be treated with agents such as those set forth herein known to be inhibitors of advanced glycosylation. Such agents would then be disposed within the filter medium in such fashion as to be in surface contact and fluid registry with smoke as it transits through the filter, to thereby capture and/or prevent the formation of advanced glycosylation endproducts. In this latter connection, the present invention extends to a filter comprising a porous medium, prepared from fibers or other like suitable materials, which has included on its active surfaces, a quantity of an agent known to inhibit advanced glycosylation or capable of trapping by reaction therewith AGEs present in the tobacco smoke stream. Such derivatized filters and filter media will find application not only in diminishing or eliminating the AGEs in the primary smoke stream generated by the direct consumption of tobacco products by smoking, but also in diminishing or eliminating the ambient AGEs attendant to environmental exposure to tobacco smoke, such as in "secondary smoking," as the inhalation by bystanders of the tobacco smoke produced in the smoking activity of others nearby has come to be called. The techniques for the preparation of such filter media are otherwise known, and do not per se form a part of the present invention. Naturally, to the extent that specific procedures will attend the application of the agents of the present invention into active position on such filter media, such techniques are, in fact, a part hereof.

A particular and important aspect of the present invention, is the discovery that tobacco and its combustion byproducts contain reactive sugars much like those observed in other foods as well as in body fluids and tissues, which exhibit toxic effects on body systems of smokers and second-hand recipients of tobacco smoke. As the curing of tobacco takes place under conditions that could lead to the formation of reactive sugars, the present inventors examined and have consequently determined that tobacco and tobacco smoke contain and disseminate these reactive species which are known to increase AGE formation in vivo. These reactive materials have been named herein "glycotoxins." As used herein the term "glycotoxins" is defined as reactive substances that may participate in, or may be formed during the Maillard reaction, which are comprised of either carbohydrate alone, or an adduct of carbohydrate and an amino-containing material, eg. protein, DNA, lipid, and all such like materials.

As demonstrated herein, glycotoxins react with protein, exhibit a specific fluorescence, crosslink proteins and are mutagenic. The data presented later herein demonstrate that tobacco smoke contains significant quantities of glycotoxins, which glycotoxins can enter the circulation and react with serum and tissue proteins to form AGEs. Increased glycotoxin exposure may contribute to the increased atherosclerosis and high prevalence of cancer in smokers, and as set forth herein, an effective therapy is believed to reside with the use and administration of inhibitors of advanced glycation, such as aminoguanidine.

The invention thus predicated on the relationship between the formation of advanced glycosylation endproducts and the preparation and consumption of tobacco. The concomitant presence of glycation reactants such as reactive sugars therein, in tobacco and tobacco smoke, and their transfer to smokers and bystanders lays the groundwork for a variety of applications, including without limitation, diagnostic and evaluative applications, therapeutic uses in connection with the inhibition of the of the accumulation of advanced glycosylation endproducts and the adverse sequelae thereof, and the treatment of tobacco materials both to potentiate their organoleptic properties and storage status, and more importantly, to reduce the deleterious effects of their use. The implementation of the principles of the present invention is facilitated by the body of research and knowledge that has resulted from the intimate investigation of the phenomenon of advanced glycosylation by the present inventors and the specific findings and observations disclosed herein.

Accordingly, it is a first object of the present invention to provide a method for the measurement of the extent and level of formation of advanced glycosylation endproducts in tobacco and its byproducts, and in the individuals who consume such products.

It is a further object of the present invention to provide a method as aforesaid that is capable of application for diagnostic purposes, to monitor the medical history of tobacco smokers and other users and to thereby avert the development of the severe pathological complications that attend the accumulation of advanced glycosylation endproducts and smoking.

It is a still further object of the present invention to provide a method as aforesaid that extends to the evaluation of tobacco to determine its storage status and organoleptic potential.

It is a still further object of the present invention to provide diagnostic assays and related materials that effectively identify tobacco-related advanced glycosylation endproducts and their presence in particular tobacco products and likewise can identify similar accumulations in consumers thereof.

It is a yet further object of the present invention to develop modifications to tobacco and tobacco products that serve to reduce the formation and transmittal of advanced glycosylation endproducts to consumers of tobacco products.

It is a further object of the present invention to provide filters to inhibit, trap or otherwise neutralize AGEs, and particularly glycotoxins, including reactive AGEs, present in tobacco smoke.

It is yet a further object of the present invention to provide methods and associated materials for evaluating the extent of risk, if any that an individual may incur as a function of the level of AGEs in the environment, to implement or adjust the treatment of such individual to avert or diminish the deleterious effects to such individual of AGE exposure.

It is a yet further object of the present invention to provide methods and associated materials as aforesaid, for use in the adjustment of the levels of said AGEs in said environment.

It is a still further object of the present invention to provide agents for the inhibition of AGEs and protein aging in tobacco users, smokers, or smoke-exposed individuals, to prevent the adverse accumulation of AGEs in said individuals and populations.

Other objects and advantages become apparent to those skilled in the art from a consideration of the ensuing detailed description which proceeds with reference to the following illustrative drawings.

BRIEF DESCRIPTION OF THE DRAWINGS

FIG. 5 is a graph showing the glycotoxins (reactive AGEs or glycation intermediates) are found in aqueous extracts of tobacco and tobacco smoke. Glycotoxins were measured in aqueous extracts of tobacco in a competitive AGE assay (A) and in a direct binding immunoassay (B). Tobacco samples from four different brands of American cigarettes were extracted in PBS for 24 hrs, filter sterilized and assayed for AGE content in the competative AGE ELISA previously described. Each bar represents a different brand of cigarette (A). Total AGE Units per cigarette were calculated as an index of the AGE content of the extracts. Tobacco samples were extracted in PBS for 1 hour, filter sterilized and assayed for reactive sugar (glycotoxin) content utilizing rat tail tendon collagen immobilized in 96-well microtiter plates (B).

(C) Glycotoxins can be removed by passing smoke through aminoguanidine. Fresh cigarette smoke was passed through a standard filter (right bar), a standard filter+500 mg sodium sulfate (middle bar) and a standard filter +500 mg aminoguanidine (left bar)

FIG. 6 is a further series of graphs showing that glycotoxins are found in cigarette smoke. (A) Glycotoxins from mainstream smoke can covalently crosslink RNAse A proteins (and this cross-linking is inhibited by aminoguanidine). RNAse A was exposed to mainstream cigarette smoke for 0, 5, 8, 24, 48 and 72 hours. To assess the formation of dimers, the samples were subjected to SDS-PAGE under reducing conditions, followed by transfer to nitrocellulose and western blotting with a rabbit anti-RNAse A antibody conjugated to HRP. Circles=RNAse A alone; Squares=RNAse A after incubation with cigarette smoke; Triangles=RNAse A after incubation with cigarette smoke and 5 mM aminoguanidine; Diamonds=RNAse A after incubation with cigarette smoke and 50 mM aminoguanidine. (B) Glycotoxins have autofluorescence. RNAse A was exposed to mainstream cigarette smoke for 0, 5, 8, 24, 48 and 72 hours and then assayed for glycotoxin-specific fluorescence by measuring emmision at 440 nm upon exictation at 370 nm. Circles=RNAse A alone; Squares=RNAse A after incubation with cigarette smoke; Triangles=RNAse A after incubation with cigarette smoke and 5 mM aminoguanidine; Diamonds=RNAse A after incubation with cigarette smoke and 50 mM aminoguanidine.

Figure 7:
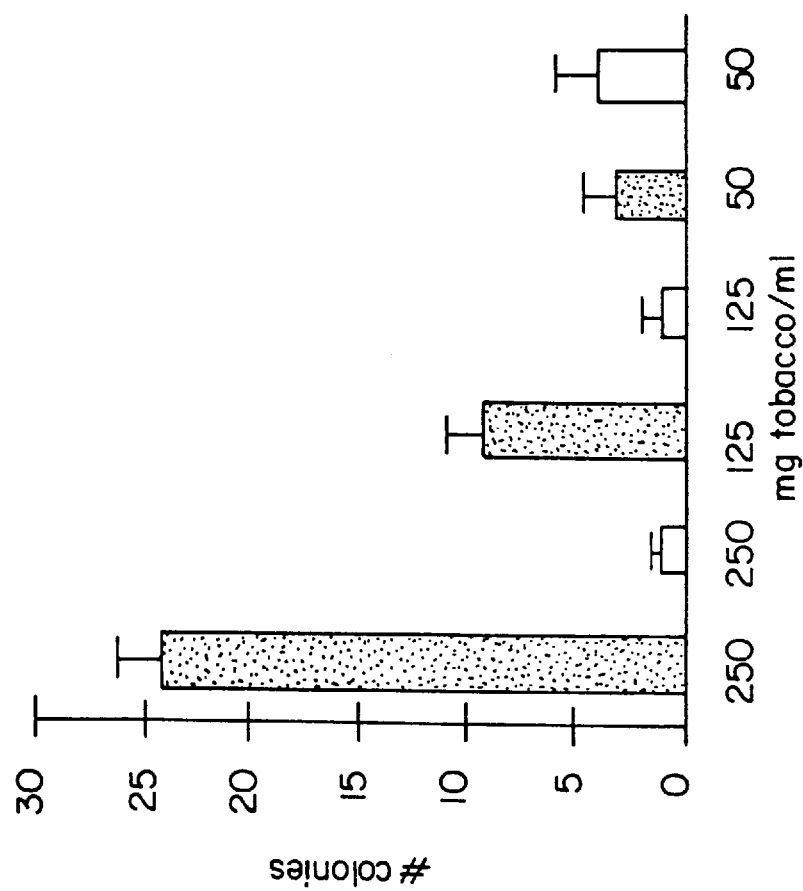

FIG. 7 is a graph demonstrating that glycotoxins are mutagenic. Salmonella strain TA98 was incubated for 1 hour with serial dilutions of condensate of cigarette smoke (Black bars), versus cigarette smoke passed through aminoguanidine (white bars) and then plated. Forty-eight hours later the number of colonies on each plate were counted. Each bar represents the mean of three plates ± standard deviation.

Figure 8A:
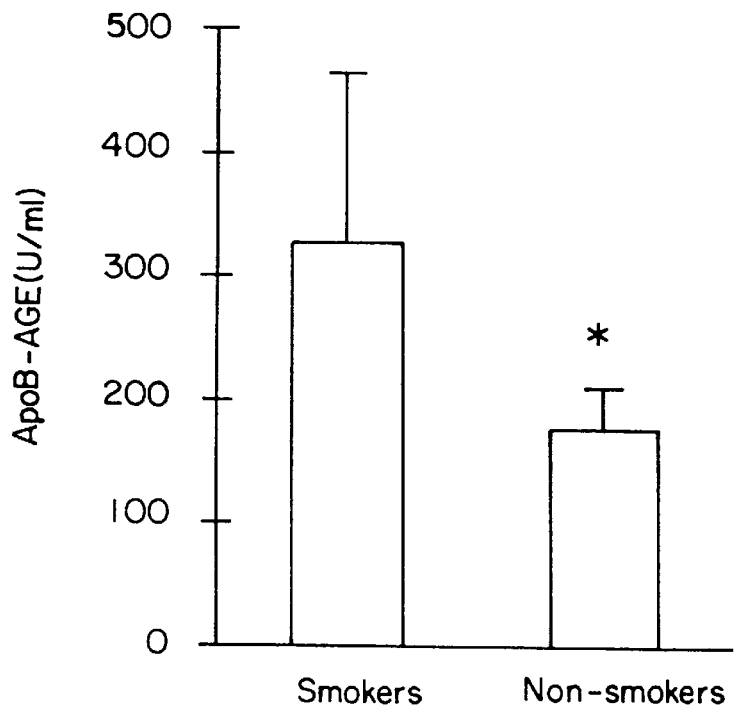
Figure 8B:
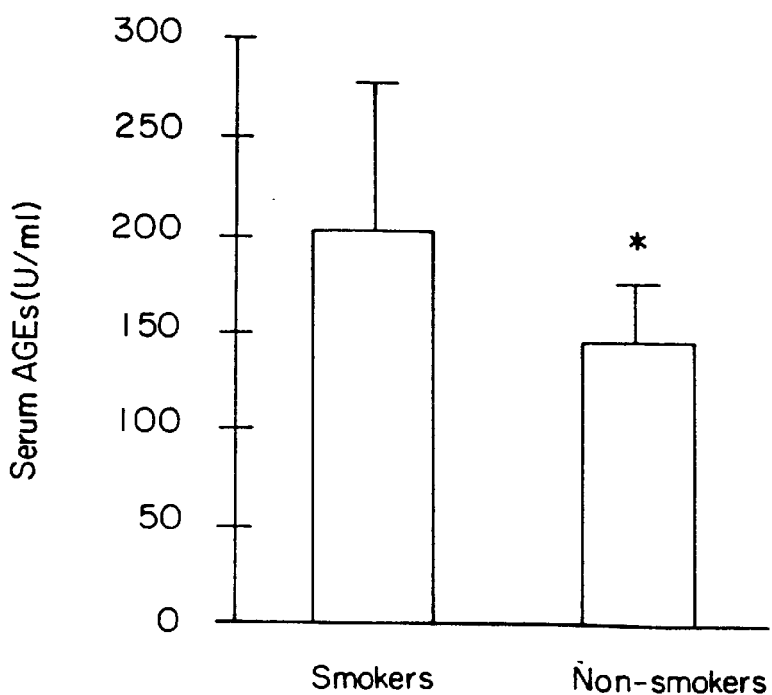

FIG. 8 is a series of graphs showing that smoking causes increased levels of apoB-AGE and serum AGE in vivo. Serum apoB-AGE (A) and total AGE levels (B) were measured in healthy non-diabetic smokers and healthy, non-diabetic, non-smokers who work at the Picower Institute. AGE-apoB levels in smokers (324±140 U/ml, n=9) were significantly higher ($p<0.01$, unpaired Student t-test) than non-smokers (177±33, n=10). [apoB-AGE>300 U/ml in diabetic patients] Serum AGE levels in smokers (202±76 AGE U/ml, n=23) were significantly higher ($p<0.02$) than the serum AGE levels in non-smokers (146±31 AGE U/ml). (serum AGE levels=200–400 in diabetics). AGE Units are expressed relative to an AGE-BSA standard. Subjects were not controlled for age, sex or number of pack-years smoked.

Figure 9:
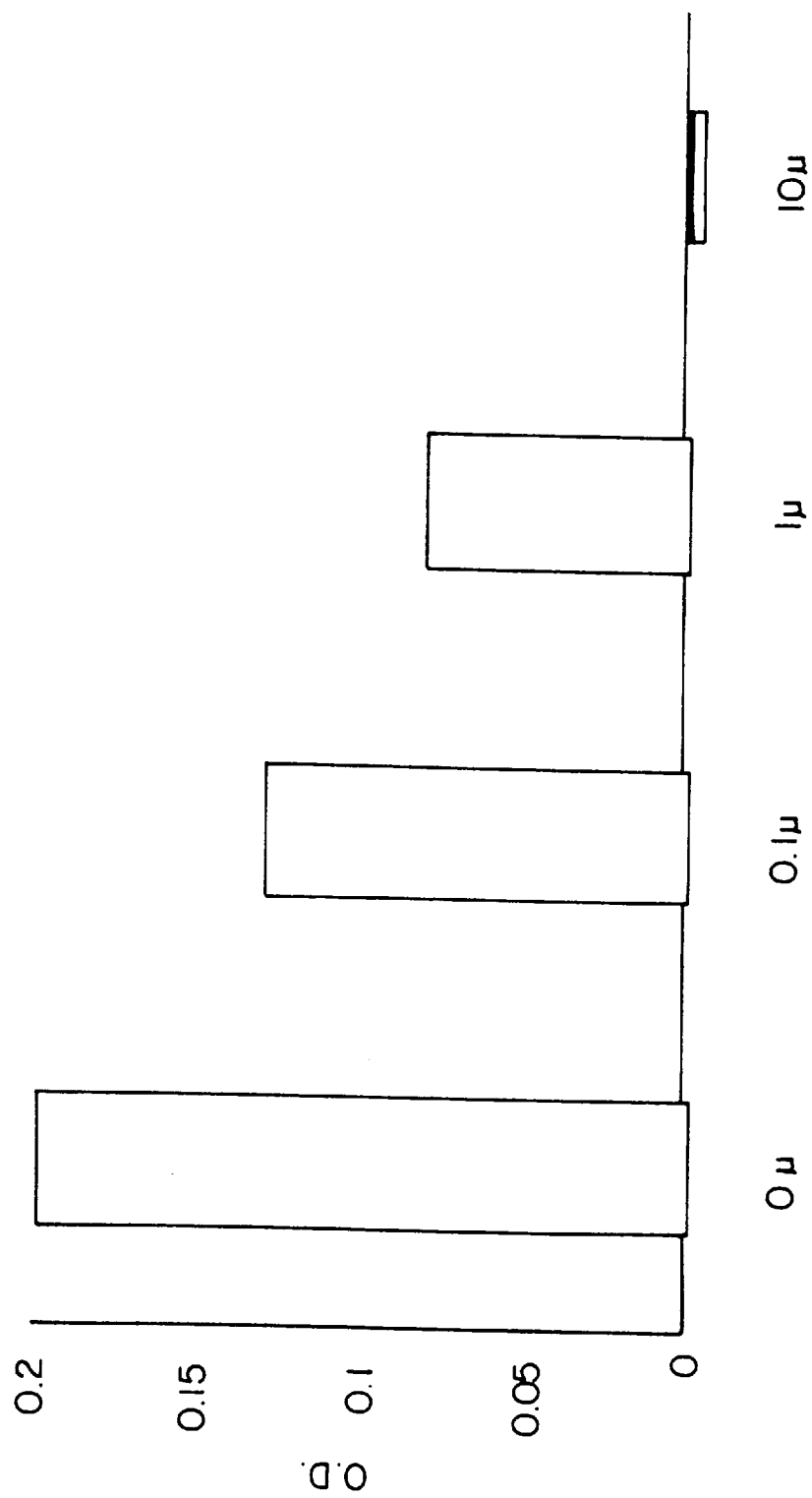

FIG. 9 is a graph showing the results of tests of tobacco that was treated by spraying with a range of concentrations of aminoguanidine, for the purpose of determining the effect of such treatment on the formation of AGEs. The tests were performed in accordance with the in vitro AGE formation assay described with reference to FIG. 6.

DETAILED DESCRIPTION OF THE INVENTION

The present invention derives from the relationship that has been identified between the consumption of tobacco and the development of increased levels of advanced glycosylation endproducts in such individuals. Initial observations resulted from investigation of levels of advanced glycosylation endproducts in a particular test population and particularly, the conjunction of increased levels of apoB-AGE and coronary heart disease in such population and the discovery of a correlation or a link with the fact that the individuals exhibiting such increased levels were regular consumers of tobacco products. The initial observation prompted the study of the tobacco products themselves, which yielded the discovery that such products, including the combustion byproduct, smoke, contained high concentrations of advanced glycosylation endproducts and the glycotoxins that promote their formation. The result of these initial discoveries has prompted further investigations and has resulted in the development of the various aspects of the present invention related to both measurement and treatment modalities with respect to tobacco, smoke, smokers, and AGEs.

More particularly, the invention extends in its initial aspect to the examination of subjects having a history of smoking to better determine their smoking history, by measuring the increases of advanced glycosylation endproducts relative to a norm derived from a non-smoking population having otherwise a similar or identical medical profile. Such methods may be practiced by the examination of a variety of body tissues and fluids of the test subject, such as blood, urine and feces. Also, the measurement of the presence and level of AGEs and glycotoxins would be useful in helping to predict the susceptibility of the test subject to diseases predicated at least in part, on the known mutagenic properties of AGEs and glycotoxins.

In similar fashion, the tobacco products themselves may be examined and evaluated to determine their potential for the promotion of increased AGE and glycotoxin levels in tobacco users. In such instance, both the tobacco product itself and its combustion byproducts may be examined for the presence of such advanced glycosylation endproducts and/or the glycotoxins that would form them. In a related aspect, the same products may be examined and the level of advanced glycosylation endproducts indexed with a view to determining the storage stability and flavor potential of a given tobacco crop. Such measurements would be developed against certain benchmarks or standards taken from like samples or populations as the case may be.

In this connection, a variety of specific implementations of the protein-browning assay and an AGE-trapping filter that may be prepared in accordance with the present invention, also provides and exemplifies the essential elements required for a smoke-exposure dosimeter convenient for the estimation of the exposure of individuals to environmental smoke, especially tobacco smoke, based on the detection of AGEs that become cross-linked to protein amino groups or other susceptible chemical glycation targets. Applicants recognize that the dilution of tobacco smoke in the atmosphere can be estimated by dosimeter devices that are formulated to capitalize on the covalent reactions that occur between tobacco smoke-related glycotoxins, AGEs and proteins or other molecules with free amino groups or other substituents that act as glycation target molecules, whereby said glycation target molecules are susceptible to chemical reaction with tobacco-related AGEs and glycotoxins, causing said AGEs and glycotoxins to become covalently cross-linked to said glycation target molecules and thereby detectable by means described herein.

The risk of exposure to environmental tobacco smoke can be estimated using a dosimeter of the present invention that exposes glycation target molecules to the atmosphere of an environment in need of monitoring for tobacco smoke burden, wherein said dosimeter provides for said reactive air-borne AGEs and glycotoxins deriving from tobacco smoke to attach spontaneously to the AGE target molecules which are displayed on a matrix, thus comprising the capture elements of the dosimeter. The AGEs that become attached to the amino group-displaying matrix of the dosimeter may be visualized, qualitatively, semi-quantitatively or quantitatively, by any of a number of AGE-identifying methods well-known in the art including, without limitation, the AGE ELISA method utilizing anti-AGE antibodies as described supra, in steps that comprise the display elements of the dosimeter. Suitable glycation target molecules for incorporation in the capture elements of the dosimeter include not only various proteins, such as BSA, RNase, collagen and poly-lysine that are well-known as AGE susceptible target molecules, but also any other biomolecules or organic compounds that present amino groups which are susceptible to reaction with AGEs.

Such glycation target molecules are preferably immobilized on the surface of a substrate which advantageously presents them to the atmosphere to be monitored; such as a paper surface derivatized to display amino groups, a nitrocellulose membrane surface similarly derivatized, a polystyrene filter surface likewise derivatized to present amino groups as glycation targets, or any other relatively inert matrix that presents glycation target molecules and is disposed to interact with the atmosphere of the environment to be monitored. Contact between the atmosphere to be monitored for tobacco smoke and the matrix-immobilized glycation target molecules, and circulation of said atmosphere over said capture elements, may be effected passively, as by convection, or actively by any means that forces the atmosphere to flow over the capture elements, such as a fan. Alternatively, the amino-group presenting glycation target molecule may be dispersed in a liquid, and air from the environment to be monitored may be drawn through said liquid, for instance by bubbling. In either case, the glycation target molecules having been exposed to the atmosphere of the environment in need of monitoring, whether disposed on a matrix or within a fluid phase, are then examined by any suitable AGE-detecting method, such as specific implementation of the general AGE ELISA assay methods disclosed infra for the detection of AGEs, such that the detection of AGEs or glycotoxins by their reaction with the glycation target molecules will indicate the degree of contamination of the environmental atmosphere with tobacco smoke. Use of such dosimeters will correspondingly indicate the exposure of individuals to secondhand smoke in the environment.

Similar methods of measurement may be employed to monitor the presence and amount of glycotoxins in tobacco products, and to thereby assess and rate their proclivity for deleterious effect on tobacco consumers and bystanders alike. For example, one may employ for such purpose the in vitro AGE formation assay presented herein to measure glycotoxins in tobacco extracts.

The dosimeters and corresponding methods of measurement recited above may be applied in a therapeutic context, to monitor and evaluate the course of treatment of a particular patient whose malady is characterized by elevated levels of AGEs in body fluids and tissues. Accordingly, a sample taken from the patient may be tested to establish the extent of reaction of AGEs present in the sample, for instance, by an AGE ELISA or like test, to apprise the treating physician of the patient's progress under treatment. The physician may then choose to modify the treatment regimen within discretion, based upon the results of the test. Equally relevantly, the measurement of both the sample taken from the patient and the ambient air in which the patient spends a preponderant amount of time, may suggest that the ambient should be remediated to reduce the exposure of the patient to additional sources of AGEs or glycotoxins, whether from tobacco smoke or other exogenous sources, and consequently, will further aid the physician in caring for the patient.

Concomitant with the above, various diagnostic assays, kits and the like may be prepared which would be specifically useful in accordance with the present invention, by the preparation of antibodies that are directed to the advanced glycosylation endproducts and glycotoxins found in tobacco and tobacco byproducts. Such antibodies may thereby be generated and thereby utilized as standards in diagnostic tests, as well as in the characterization of tobacco-related AGE and glycotoxin chemical structure.

With regard to therapeutic strategies and agents covered by the present invention, the correlation between increases in advanced glycosylation endproducts and the use of smoking materials prompts the application of therapeutic methods already identified with respect to the treatment of conditions in which the increase in levels of advanced glycosylation endproducts is believed to play a role. Such methods, therefore, would be applicable in the present instance, as where a particular individual has a history of tobacco product consumption, and where accordingly, a method of treatment might involve the administration of inhibitors of advanced glycosylation endproducts for such individual.

Suitable inhibitors of advanced glycation have been identified earlier, and include, for example, aminoguanidine (Pimagedine), its analogs, agonists, congeners, cognates and mimics and mixtures thereof where appropriate. Other suitable inhibitors may be selected from among those active aldehydes, or compounds bearing a correspondingly active aldehyde substituent, that are reactive with the glycosylamino moiety of the early Amadori and Heyns products of the Maillard reaction, as identified supra, and mixtures and combinations thereof where appropriate. Additional suitable inhibitors may be selected from those thiazolium derivatives and other compounds and compositions thereof identified supra, which are reactive with $\alpha$-dicarbonyl segments within existing AGEs, especially those of such compounds which promote or initiate cleavage of said $\alpha$-dicarbonyl segments within said existing AGEs in a self-regenerating, catalytic fashion. The exact mode of administration would be upon the determination of a skilled physician.

An alternative strategy with respect to smokers would be the direct treatment of the smoking materials that are being consumed. Such materials could be treated by similar inhibitors, so that the tobacco products receiving such treatment would have a reduced number of AGEs (and particularly a reduced number of glycotoxins and reactive AGEs), or a reduced capacity to promote the formation of such AGEs in the consumers.

Alternatively, the invention extends to the preparation of filter materials that could be embodied in tobacco products such as cigarettes, so that the filters themselves would be capable of inhibiting, trapping, or otherwise neutralizing tobacco-related AGEs or related chemical entities that promote increased formation and transmittal of advanced glycosylation endproducts (eg. glycotoxins). The filter materials in turn are those that are conventionally provided and are fabricated for use in cigarettes, and are frequently fibrous material bundled together and bound into a cylindrical form in the finally assembled cigarette. Such fibrous materials, of which cellulose fibers are representative, could contain on their surfaces an appropriate inhibitor or reactive agent that would serve to trap AGEs or to otherwise bind to or neutralize other glycation products such as glycotoxins, so as to prevent them from forming AGEs upon consumption.

In an alternative embodiment, filters active in inhibiting, trapping, or otherwise neutralizing tobacco- or smoke-related AGEs or related entities that promote increased formation and transmittal of advanced glycation endproducts can be fabricated for use in general or environmental air purification, for instance to diminish or eliminate the ambient atmospheric AGEs and/or glycotoxins that would otherwise be undesirably consumed by indirect, passive or "secondhand" smoking. Such filters or like materials may be prepared to enable the sampling of the environment, whether by contact with ambient air, or by direct application to such materials or substrates to samples, biological or otherwise, where concentrations of AGEs or the glycotoxins that may form them, are suspected; for the purpose of instituting measures to reduce such AGE levels. Such measures may comprise the appropriate treatment of the environment to remediate those areas where AGE levels are undesirably elevated, or to institute or adjust the treatment of individuals located in that environment to reduce the internal AGE level or burden in such individuals. Particular such therapies include the administration of agents such as those referred to herein, that function as inhibitors of AGE formation, or that function to promote or effect the removal of AGEs from the body.

In their general formats and in a variety of specific implementations, the protein-browning assay and the AGE-inhibiting, AGE-trapping or AGE-neutralizing filters of the present invention also provide and exemplify the essential elements required for smoke-exposure dosimeters convenient for the estimation of the exposure of individuals to environmental smoke, especially tobacco smoke, based on the detection of AGEs that become cross-linked to protein amino groups or other susceptible chemical glycation targets. Applicants recognize that the dilution of tobacco smoke in the atmosphere can be estimated by dosimeter devices that are formulated to capitalize on the covalent reactions that occur between tobacco smoke-related AGEs and/or glycotoxins, and proteins or other molecules with free amino groups or other substituents that act as glycation target molecules, whereby said glycation target molecules are susceptible to chemical reaction with tobacco-related AGEs, causing said AGEs to become covalently cross-linked to said glycation target molecules and thereby detectable by means described herein. The following examples are provided as illustrative of the experiments that have been performed to identify this relationship and to facilitate the implementation of the above inventive embodiments.

EXAMPLE 1

Figure 1:
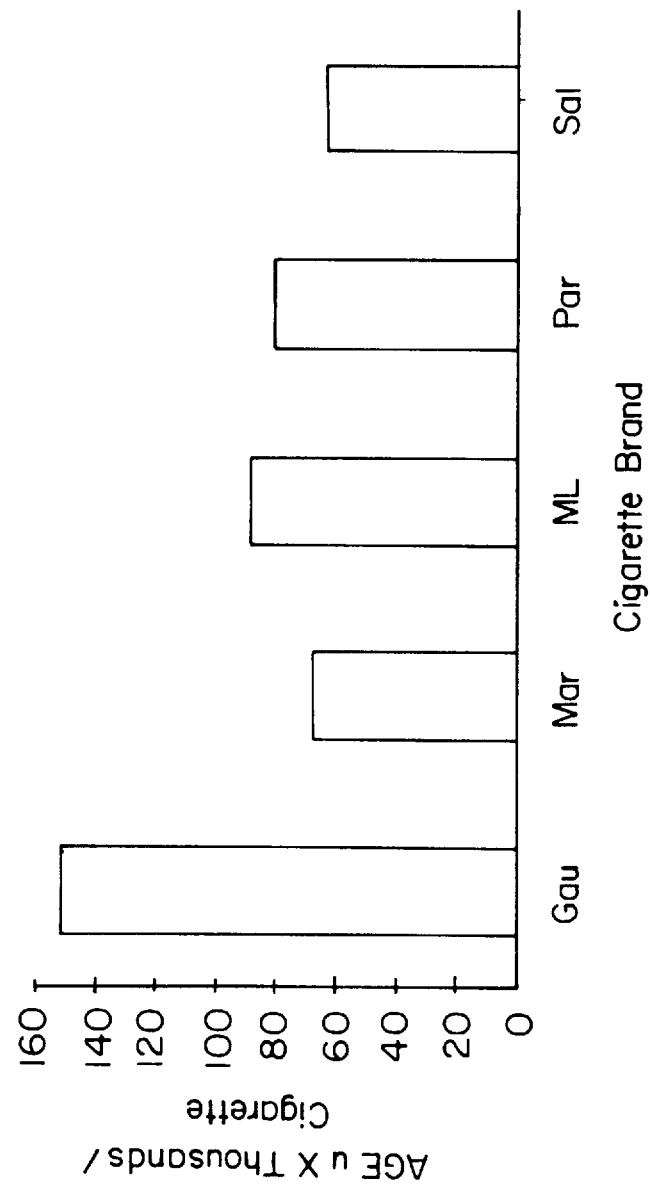
FIG. 1 is a graph showing the AGE content of aqueous extracts of cigarette tobacco. AGE levels in phosphate buffer extracts of cigarette tobacco samples were quantified in a standardized competitive AGE immunoassay and calculated as Total AGE Units per Cigarette. Cigarette brands were: Gau, Gauloises; Mar, Marlboro; ML, Marlboro Light; Par, Parliament; Sal, Salem Ultra Lights.

To determine whether AGEs are present in tobacco products, tobacco samples from several commercially available cigarette brands were prepared in 0.02M phosphate buffer, pH 7.4, at a tobacco concentration of 66.7 mg/ml. After an overnight incubation at room temperature, the tobacco was pelleted by centrifugation and the aqueous tobacco extract was filter sterilized, diluted 1:800, and analyzed for AGE content. Dilutions of the aqueous tobacco extracts were assayed for AGE content in a standardized competitive AGE immunoassay utilizing an anti-AGE monoclonal antibody (see below), which assay measures Units of AGE immunoreactivity relative to a reference standard competitor preparation of AGE-modified bovine serum albumin (AGE-BSA). From the assay results, Total AGE Units per Cigarette were calculated as an index of the AGE content of the tobacco, and, as shown in FIG. 1, the extractable AGE content of these tobacco samples ranged from about 50,000 to 150,000 AGE Units per cigarette. From this evidence, Applicants concluded that extremely high AGE-like immunoreactivity is present in aqueous extracts of tobacco. This suggested to Applicants that consumers of tobacco products including, for instance, snuff and chewing tobacco, or the smoke from combustible forms such as cigars, cigarettes or pipe tobacco, may be exposed to AGEs in large amounts through their tobacco consumption. Furthermore, since AGEs are known to accumulate over time in a temperature- and sugar-dependent manner, and since AGEs are known to contribute to taste and flavor, this information also suggested to Applicants that the AGE content of specific tobacco lots or crops might be a useful indicator of the flavor potential, and of the storage and curing history, of tobacco during its commercial processing into various consumer products and subsequent marketing.

A competitive ELISA for AGEs is conducted according to general immunoassay procedures that are common in the art. Briefly, a Master Stock of AGE-modified BSA (AGE-BSA) was prepared by incubating BSA (Calbiochem, Cat. #12657, Fraction V, purity >99% by SDS-PAGE) at 50 mg/ml in 0.5M glucose prepared in phosphate-buffered saline (PBS), pH 7.4, containing 1.0 mM EDTA and overlaid with a nitrogen atmosphere in sealed tubes for eight weeks at 37° C. Commercially available 96-well microtiter assay plates (NUNC Maxisorp) are coated with the standard antigen by incubating 100 $\mu$l of a solution of AGE-BSA at a concentration of 30 $\mu$g/ml in Coating Buffer (0.1M NaHCO$_3$/0.02% azide, pH 9.6) in each well overnight at 4° C., covered. Assay wells are then rinsed six times with 200 $\mu$l Wash Buffer (Tris-buffered saline with 0.05% Tween 20) using an automated ELISA plate washer, inverted, and blotted to dry. Each well then receives 200 $\mu$l Blocking Buffer (PBS/2% normal goat serum/0.2% BSA/0.02% azide, pH 7.4) and the plate is incubated, covered, for 1 hour at 37° C. After a rinsing as above, the standard AGE-BSA-modified assay plate is ready for use in the competitive ELISA.

The assay method of the present Example was initiated by addition of a 50 $\mu$l aliquot of sample or AGE-BSA Standard Competitor to each well of an AGE-BSA-coated assay plate, followed by the immediate addition 50 $\mu$l of an appropriately titrated preparation of an anti-AGE antibody. The plate was then incubated, covered, for two hours at room temperature, during which period AGEs within the test sample (or the AGE-BSA standard) competed for binding with the primary or anti-AGE antibody against the AGEs immobilized on the assay plate in the form of AGE-BSA. Ultimately, in this competitive immunoassay format, higher amounts of AGEs in the sample are reflected in higher competition against the coated AGE-BSA with corresponding diminishment of the final readout signal, the intensity of which reflects the degree of binding of the primary anti-AGE antibody to the AGE-BSA-coated well. In this example, an anti-AGE monoclonal antibody, designated 4G9, was used at a dilution that provided approximately 1.5 optical density (OD) Units after the two hour final incubation with the chromogenic substrate in wells that received no competitor. A dilution series of AGE-BSA Standard Competitor was prepared by diluting AGE-BSA Master Stock to provide a concentration series ranging from about 0.1 to 2 $\mu$g AGE-BSA per well, and the equivalent concentration of AGE-BSA Standard Competitor corresponding to the final OD of each sample well could be interpolated from this standard competition curve. One AGE Unit is operationally defined as the concentration of Standard Competitor AGE-BSA (in BSA mg/ml) required for 50% inhibition in this competitive AGE ELISA format.

After this incubation of primary antibody and competitor (sample or standard), the wells were rinsed six times with Wash Buffer, inverted and blotted to dry. A commercially available preparation of secondary antibody-enzyme conjugate (for instance, anti-mouse IgG antibodies raised in goat, coupled to alkaline phosphatase) is then added and incubated according to the manufacturer's recommendations, typically as a 100 $\mu$l aliquot at a dilution of 1:1200 for 45 minutes at 37° C. Of course a variety of primary (anti-AGE) antibodies, either polyclonal or monoclonal or a mixture thereof, as well as a variety of means of detecting the binding of these primary antibodies, can be substituted in this procedure by relying on general immunoassay principles well understood in the art.

In the present Example, the plates were then rinsed as above and a 100 $\mu$l aliquot of substrate chromogen (in this case, para-nitrophenyl phosphate (PNPP)) was added at a concentration recommended by the manufacturer and incubated, typically at 37° C. for 1–2 hours, to provide an OD of 1.5–1.7 Units in the control wells assayed in the absence of any competitor. Absorbance (OD) in each well may be read conveniently using a commercial microtiter plate reader, in this instance set to read at 410 nm versus a reference wavelength of 570 nM. The AGE level in any sample may then be interpolated as the equivalent concentration of Standard Competitor AGE-BSA (in BSA mg/ml) from the standard competition curve, and this value is then typically converted into AGE Units where 1 AGE Unit is the concentration of Standard Competitor AGE-BSA that produces 50% inhibition in this competitive AGE ELISA method.

EXAMPLE 2

Figure 2:
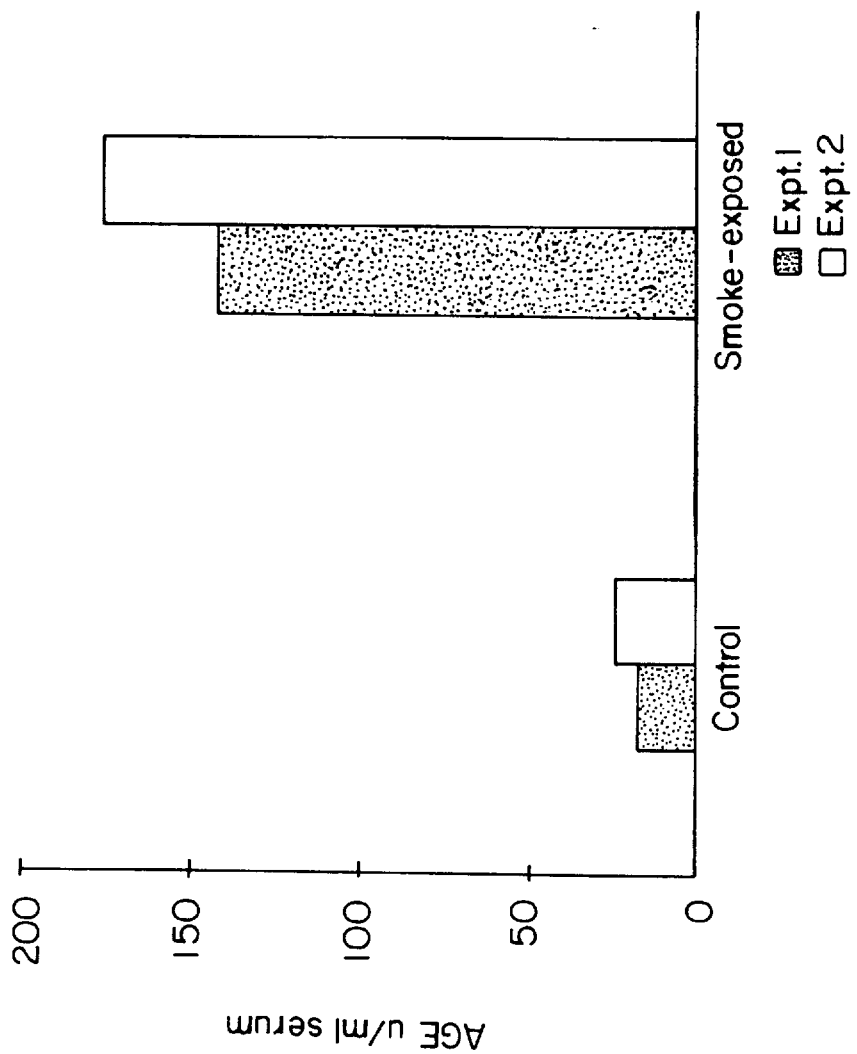
FIG. 2 is a graph showing AGE levels in serum experimentally exposed to tobacco smoke. AGE levels in serum samples through which cigarette smoke was bubbled were quantified in a standardized competitive AGE immunoassay and calculated as AGE Units per ml Serum. Control=a similar serum sample exposed only to an airstream, without tobacco smoke.

To determine whether the glycotoxins (reactive sugars, AGEs, etc.) present in tobacco smoke are reactive with the body's proteins, cigarette smoke was drawn through a 1 ml sample of normal human serum using a "hookah" or waterpipe smoking device constructed from a small glass sidearm flask which was designed and operated not only to bubble a stream of smoke through the contained serum sample, but also to allow smoke to accumulate above, and in contact with, the serum sample, which exposure was maintained during an incubation period following the active "smoking" phase of exposure. Filters were removed from the cigarettes to be used, and a cigarette was mounted in a Pasteur pipette that penetrated the stopper of the flask to terminate with its tip submerged in the serum sample. Once assembled, this device was repeatedly operated to draw the smoke from five (5) cigarettes through the serum sample by suction applied with a syringe attachable to the sidearm. Approximately the same volume of air was drawn through a separate serum sample using an identical device except that no cigarette supplied smoke to the airstream for this control reaction. AGE levels in these experimentally treated serum samples were then measured by the standardized competitive AGE ELISA described above (see Example 1). This experiment was conducted twice independently, with comparable results in each case as shown in FIG. 2. Thus, while control serum samples averaged less than 25 AGE Units per ml, smoke-exposed serum samples showed about 150 AGE Units per ml. From this evidence, Applicants concluded that the AGEs present in tobacco smoke were reactive and were likely to attach to human proteins during smoking (either active or passive), increasing the AGE burden of smokers and bystanders, and providing by reference to a suitable control sample from a smoke-free population, a ready marker of the intensity of their recent smoking activity, or of their recent environmental exposure to tobacco smoke.

EXAMPLE 3

In a further test to determine whether reactive sugars, glycotoxins, etc. are present in tobacco smoke, and to determine whether such glycotoxins can react with proteins to form AGEs, condensates of tobacco smoke were assessed for reactive AGE content as follows. A sidearm flask was equipped with a stopper to which was fitted a short piece of rubber tubing with an Pasteur pipette attached. A syringe fitted to the sidearm was operated repeatedly to draw smoke from a total of 3–5 cigarettes into the flask, which was immersed during this period of smoke condensate collection in an acetone/dry ice bath. Cigarette smoke condensed on the walls of the chilled flask, and this condensate material was solubilized and extracted into warm neutral aqueous solution by rinsing the interior of the flask with five mls of 0.02M phosphate buffer. This condensate extract was filter sterilized and diluted 1:5 with additional phosphate buffer.

The presence of glycotoxins in these extracts was then assessed in an AGE formation assay that uses anti-AGE antibodies to detect the covalent attachment of AGEs to an immobilized collagen layer. Briefly, commercially available 96-well micro titer plates with rat tail tendon collagen immobilized on the surface of the wells (Collaborative Research) were exposed to dilutions of the smoke condensate extracts described above and incubated overnight, covered, at room temperature. AGEs that become immobilized on the surface by interaction with the tail tendon collagen are then assayed in accordance with the immunometric procedures outlined above for the competitive AGE assay: smoke extract-treated collagen-coated plates were sequentially rinsed, exposed to the 4G9 monoclonal anti-AGE antibody, rinsed, exposed to a commercially available goat anti-mouse IgG/alkaline phosphatase conjugate, rinsed, and supplied with an appropriate chromogenic substrate (e.g. PNPP) to generate a signal measured by optical density at 410 nm which quantitatively reflects the amount of AGE-like immunoreactivity that had accumulated on the plate by exposure to the tobacco smoke condensate extract relative to controls not treated with smoke condensate extract.

Figure 3:
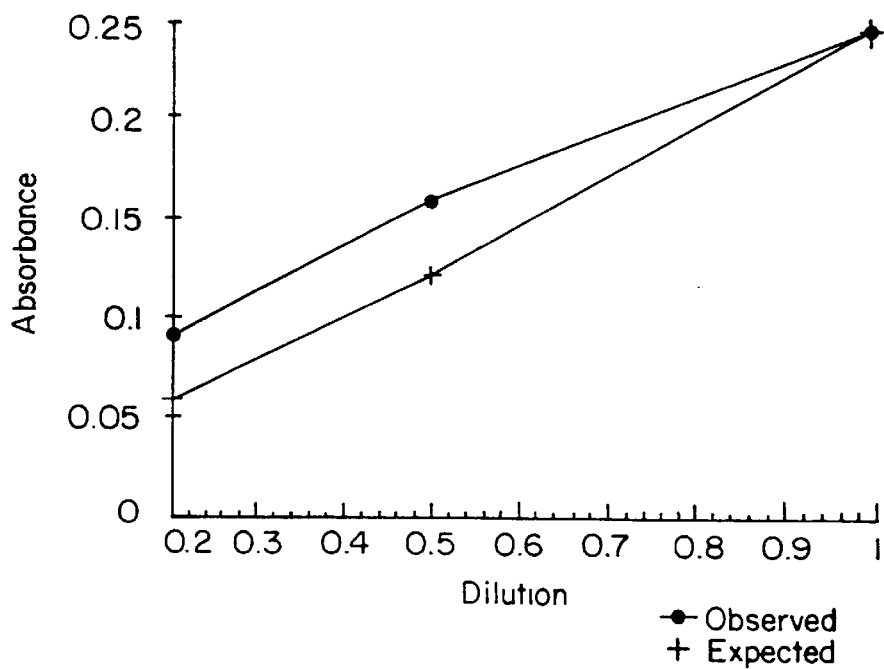
FIG. 3 is a graph showing that glycotoxins, and reactive sugars and AGEs present in aqueous solutions of condensates of tobacco smoke are reactive with proteins in vitro. Collagen-coated assay plates were exposed to phosphate buffer-solubilized condensates of cigarette smoke, and AGEs formed on the collagen-treated assay plate wells were measured by an immunometric method whereby an increase in the final absorbance (optical density or OD) reflects increased AGE crosslinking to, and accumulation on, the collagen matrix of the assay plate.

As shown in FIG. 3, there is more AGE-like immunoreactivity in wells exposed to tobacco smoke condensate extract, and the signal from these smoke-related AGEs decays with dilution of the extracts in close conformity with the dilution of glucose-derived AGEs formed in vitro as a standard for such comparisons. This indicated to Applicants that exposure to tobacco smoke will correspondingly expose the subject to glycotoxins that are reactive with natural proteins.

Figure 4:
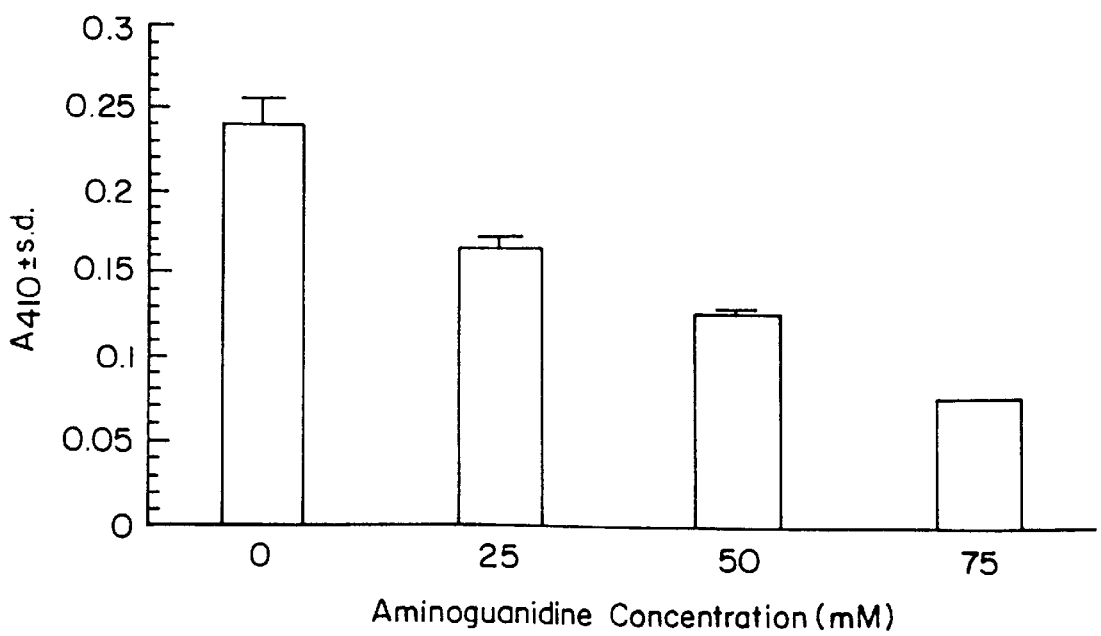
FIG. 4 is a graph showing that Pimagedine (aminoguanidine) inhibits the in vitro reaction of cigarette smoke condensate extract with protein. Collagen-coated assay plates were exposed to aqueous extracts of condensates of cigarette smoke in the presence or absence of various concentrations of Pimagedine. AGEs formed on the collagen-treated assay plate wells were then measured by an immunometric method whereby an increase in the final absorbance (optical density or OD) reflects increased AGE crosslinking to, and accumulation on, the collagen matrix of the assay plate.

In a supplemental series of experiments, Pimagedine (aminoguanidine), an AGE inhibitor active, among other things, in inhibiting AGE crosslink formation, was included at various concentrations during the overnight incubation of tobacco smoke condensate extracts in the rat tail tendon collagen-treated plates. As shown in FIG. 4, Pimagedine decreased the amount of AGEs detected immunometrically in a dose-dependent fashion with about a 50% inhibition at about 50 mM Pimagedine. This inhibition or diminishment of the final AGE signal as a result of the presence of this AGE-inhibiting pharmacological agent is a further indication that the AGE-like immunoreactivity that is apparent after experimental treatment of tail tendon collagen with smoke condensates resembles in molecular detail the AGEs that form spontaneously on proteins in vitro and in vivo with exposure to reducing sugars, in that AGEs from all of these sources share immunochemical determinants and their formation and/or crosslinking activity is specifically inhibitable by Pimagedine. This evidence that the reactive AGEs present in tobacco smoke can be inhibited by Pimagedine also suggested to Applicants that a corresponding anti-AGE intervention by treatment either of tobacco, tobacco smoke, or tobacco smokers would serve to decrease the excess AGE burden to which smokers expose themselves by their tobacco consumption.

EXAMPLE 4

A series of experiments were performed to further investigate and demonstrate the the relationship between tobacco and its combustion byproduct, tobacco smoke, and the incidence of elevations in the formation of AGEs. Particularly, and as set forth herein, the experiments establish that tobacco and its byproduct contain a significant amount of soluble reactive glycation intermediates, named herein glycotoxins, that promote AGE formation and the full menu of secondary molecular and physiological complications associated with AGE accumulation in aging and diabetes, and that are mutagenic, and consequently may participate in the promotion of pathologies such as cancer. The protocols and subsequent experiments follow below.

Materials and Methods
Preparation of aqueous tobacco extracts.

Tobacco samples were extracted in PBS at a concentration of 360 mg/ml for 1 hour with agitation and filter sterilized through a 0.45 $\mu$m Millex-HA filter unit (Millipore, Bedford, Mass.).

Preparation of cigarette smoke condensate

A "water-pipe" smoking device was designed and operated to allow a stream of smoke to come into contact with an aqueous solution. An aqueous solution (3 mls) was placed in a 25 ml glass erhlemeyer flask with a sidearm, cigarettes were mounted in a 500 ul pipette tip that penetrated a hole in the stopper of the flask. The tip of the 500 ul pipette tip extended down past the opening of the sidearm of the flask, but did not penetrate the aqueous solution. Once the device was assembled a vacuum (approx. 20 mm Hg) was applied to the sidearm of the flask and the cigarette was lit. In some experiments the pipette tip was modified: A 2 mm×2 mm piece of commercial cigarette filter was used to plug the tip of the pipette tip and then 500 mg of either nothing, aminoguanidine hydrochloride or sodium sulfate was placed between the small piece of filter and the cigarette. The pre-attached commercially prepared filters were not removed from the cigarettes in any of the experiments. Five cigarettes were smoked into each 3 ml aliquot of PBS. Before use the aqueous cigarette smoke condensate was filtered through a 0.45 um Millex-HA filter unit (Millipore).

In vitro AGE formation assay.

Microtiter plates containing immobilized rat tail tendon collagen (Collaborative Research, Cambridge, Mass.) were incubated with TBS (PBS/0.05% Tween-20) for 1 hour, then incubated with serial dilutions of either the tobacco extract or smoke-exposed PBS solution for 18 hours at 37° C., washed five times with TBS, incubated with a rabbit polyclonal anti-AGE sera (pAb RU 9.9.93 diluted in TBS/0.1% goat serum) for 1 hour, washed five times with TBS and incubated with anti-rabbit IgG conjugated to alkaline phosphatase (Sigma) and washed five times with TBS. Then, bound AGEs are revealed by incubating with 250 mg/ml p-nitrophenyl phosphate in 100 mM diethanolamine pH 9.5 for 45 minutes and plates were read at 405 nm on an ELISA plate reader (Dynatech, MR 5000). Biolynx 2.0 was used for generation of a standard curve and data extrapolation.

Glycotoxin crosslinking activity.

A solution of PBS containing 2 mM EDTA was exposed to cigarette smoke as described above. 40 mg of RNAse A dissolved in PBS/EDTA containing either 0, 5 or 50 mM aminoguanidine was exposed to the equivalent of 8 cigarettes and incubated at 37° C. in the dark for 0, 5, 8, 24, 48 and 72 hours. Unbound and low molecular weight materials were removed using a Centricon 10 concentrator (Amicon, Beverly, Mass.). To assess the formation of RNAse dimer formation, samples were subjected to discontinuous SDS-PAGE under reducing conditions using a 5% stacking gel and a 12% resolving gel [*Nature* 227: 680–685, 1970] and transferred to nitrocellulose paper. The blot was blocked with blocking solution (PBS/5% non-fat milk/1% BSA/0.2% Tween-20) for 1 hour at 20° C., incubated with rabbit anti-ribonuclease A antibody conjugated to horseradish peroxidase (Biodesign International, Kennebunkport, Me.) diluted in blocking solution for 45 minutes, washed extensively with PBS/0.2% Tween-20 and developed according to the manufacturer's directions. The resulting fluorograph was processed using Adobe Photoshop and densitometric measurements of images (smoothed, sharpened and contrast enhanced) determined using the NIH image program.

Fluorescence determinations

To assess AGE specific fluorescence the emission at 440 nm upon excitation at 370 nm using a LS 50B fluorescence spectrometer (Perkin-Elmer) was measured in the samples of RNAse exposed to cigarette smoke condensate (preparation described above). Fluorescence values were measured at a protein concentration of 0.5 mg/ml.

Mutagenicity studies

The mutagenicity assay was performed as described by Ames et al. [ ] Briefly, Salmonella strains TA98, TA100, TA1535 and TA1537 (gift from Dr. B. N. Ames) were cultured overnight at 37° C. in Oxoid nutrient broth (Difco), incubated with serial dilutions of cigarette smoke condensate in 0.1M sodium phosphate buffer, pH 7.4, in triplicate for 1 hour and then plated on minimal glucose plates at a concentration of 0.1 ml/plate. The plates were then incubated overnight at 37° C. and the number of revertant mutants on each plate was counted.

Serum AGE-apoB measurement

The amount of AGE-modified apoB (AGE-apoB) was measured in human serum by sandwich ELISA employing a monoclonal anti-AGE capture antibody and an anti-apoB-HRP conjugate as described previously (*JBC,* 267: 5133–5138, 1992). The samples were assigned a value from the standard curve and expressed in apoB-AGE U/ml of serum. One Unit of apoB-AGE is defined as the activity of 1 $\mu$g of apoB (LDL).

AGE Measurement

AGEs in human sera were measured by a competitive ELISA employing an AGE-specific monoclonal antibody (IgGI subclass) raised to a glucose-derived AGE epitope as previously described in (*PNAS USA* 90: 6434–6438 and infra). AGE-immunoreactivity was determined in triplicate wells for samples which were serially diluted to fall within the linear range of the assay. AGE Units were calculated relative to a synthetic AGE-BSA standard. The assay sensitivity was 5 U AGE /ml and the intra- and inter-assay coefficient of variation was 5% and 8% respectively.

Results

Aqueous extracts of tobacco and cigarette smoke contain glycotoxins which promote AGE formation in vitro.

Initially, the water soluble reactive glycotoxins were extracted from cigarette tobacco samples by soaking in PBS. To test whether or not the glycotoxins in tobacco were capable of inducing AGE formation, the aqueous extract was added to collagen-coated plates for 18 hours. The presence of newly formed AGEs on the collagen molecules was detected using a specific anti-AGE polyclonal antibody. FIG. 5A shows a comparison of the AGE formation induced by eight brands of American cigarettes. Extracts from all brands tested promoted the formation of AGE moieties. It is interesting to note that brand E, the "light" equivalent of cigarette brand D, contained more of such AGE-forming activity than brand D. This finding, which was consistently reproduced when other "regular" and "light" brand pairs were compared, probably reflects a difference in the processing of the tobacco and indicates that tar content and other measures of cigarette "strength" are independent of glycotoxin content.

To determine if the tobacco-derived glycotoxins could be volatilized, we tested cigarette smoke condensate in the AGE formation assay. To collect any volatile glycotoxins, we set up a smoking apparatus in which smoke from a burning cigarette was drawn into a flask containing a PBS solution. In an attempt to more closely simulate the way in which lung tissue is exposed to cigarette smoke, experimental smoke was permitted to come into contact with the PBS in the bottom of the flask, but not bubbled through the solution. Immediately after preparation, the smoked-exposed PBS (cigarette smoke condensate) was added to microtiter wells coated with collagen and allowed to react overnight. Like the aqueous tobacco leaf extracts, cigarette smoke condensate was able to rapidly induce the formation of AGEs that were recognized by the rabbit anti-AGE polyclonal antisera. The production of AGEs by the cigarette smoke was concentration (FIG. 5B) and time (data not shown) dependent and could be inhibited in a dose-dependent manner by adding a soluble AGE inhibitor, aminoguanidine, directly to the wells (data not shown) or by passing the smoke through a column of aminoguanidine crystals (FIG. 5C). Passing the smoke through a control column of sodium sulfate had no effect on the ability of the smoke-borne tobacco-derived glycotoxins to form AGEs on the target (FIG. 5C). The cigarette smoke condensate was approximately ten-fold less active at promoting AGE formation than the aqueous tobacco extracts, which suggests that either some of the glycotoxins are destroyed by the burning process or that the system for capturing the volatile glycotoxins and AGEs is inefficient. The AGE forming activity found in both the tobacco leaf extract and the cigarette smoke condensate was labile: it was undetectable if the solutions were frozen at −20° C. and thawed before testing, or left sitting on ice or at room temperature for greater than 5 hours.

The ability of cigarette smoke glycotoxins to induce AGE formation was also assessed by measuring the characteristic fluorescent pattern of AGEs on RNAse A exposed to cigarette smoke condensate. As shown in FIG. 6A, RNAse A exposed to cigarette smoke condensate for increasing amounts of time exhibited a time-dependent increase in AGE-typical fluorescence, (i.e., emission at 410 after excitation at 370 nm), that reached saturation after 24 hours and was inhibited by the presence of aminoguanidine during the incubation.

Glycotoxins can cross-link proteins

One of the hallmarks of reactive reducing sugars is that they promote the formation of intra- and inter-molecular crosslinks between the susceptible functional groups. To show that the reactive glycotoxins in tobacco and tobacco smoke also had this property, we assayed glycotoxins for their ability to crosslink RNAse A. Samples of RNAse A were incubated with cigarette smoke condensate for various amounts of time, separated by molecular weight on an SDS-PAGE gel and then visualized with anti-RNAse A antisera. Using this technique, Applicants were able to determine that RNAse A-RNAse A dimer formation was time dependent and reached saturation within 24 hours. Dimer formation could be inhibited by aminoguanidine in a dose-dependent manner, indicating that the crosslinking process was dependent on carbonyl-containing glycotoxins (FIG. 6B).

Glycotoxins are mutagenic

Previous studies have shown that reducing sugars can react in vitro with DNA and induce mutations in both bacterial and mammalian cells. High intracellular concentrations of the reducing sugar, glucose-6-phosphate, in *E. coli* leads to an increased mutation rate. Similarly, murine fetuses exposed to high blood sugar concentrations due to maternal diabetes exhibit a doubled mutation rate.

In the present experiments, a number of strains of *Salmonella typhimurium* (TA98, TA100, TA1535 and TA 1537) were exposed to cigarette smoke condensate in the manner of a typical Ames mutagenesis test. A brisk mutation activity was noted in strain TA98, but not in the other strains. As can be seen in FIG. 7, the exposure of TA98 to increasing amounts of freshly prepared cigarette smoke condensate resulted in a dose-dependent increase in mutations. When TA98 is exposed to a mutagenic agent that is able to cause a frameshift mutation and thereby reverse the original mutation in the histidine operon, it will grow on histidine-deficient media. The passage of the smoke through a dry column of aminoguanidine prior to the contact with the PBS (which apparently removed or neutralized the carbonyl-containing glycotoxin molecules) decreased the number of revertant mutants. Similar mutagenic activity has been seen in the reaction of DNA with reducing sugars noted above. This is the first report of which the applicants are aware of a mutagenic activity in cigarette smoke which does not require metabolic activation by the P450 system. This activity may have been missed in the past, as previous workers have prepared predominantly smoke extracts in organic solvents and analyzed the mutagenic activity after considerable periods of time. The lability of the glycotoxins in the aqueous extracts required the rapid analysis of the mutagenic activity. Aqueous cigarette smoke condensates which were allowed to incubate either at room temperature or on ice for more than five hours were no longer mutagenic.

Glycotoxins promote the formation of AGEs on serum proteins in vivo.

The possibility was next investigated that the reactive glycotoxins or AGEs could be absorbed in vivo following exposure to cigarette smoke by examining the amount of AGEs that were formed on serum proteins as a surrogate marker for total body burden.

Blood samples from otherwise healthy smokers and non-smokers

In this study AGE serum protein levels and protein apoB-AGE were assayed. The AGE-apoB levels in smokers ($324\pm140$ U/ml, n=9) were significantly higher (p<0.01, unpaired Student t-test) than non-smokers ($177\pm33$, n=10) and the serum AGE levels in smokers ($202\pm76$ AGE U/ml, n=23) were significantly higher (p<0.02) than the serum AGE levels in non-smokers (146±31 AGE U/ml). All individuals in the smoking group smoked more than 1 pack per day, but otherwise their smoking history was not controlled for. Similar studies would correlate the amount of AGE attached to apo-B or other serum proteins present in the blood with the degree of exposure to cigarette smoke. This integral of exposure will allow analysis of exposure to first- and second-hand smoke. In effect, this test would be similar to the hemoglobin $A_{1C}$ test which gives an integral of the blood glucose exposure for the preceding 30 day period. It is interesting to note that the levels of AGE-serum proteins and AGE-apoB in smokers are nearly the same as those seen in patients with diabetes [AGE-serum proteins 200–400 U/ml; AGE-apoB 300 U/ml].

EXAMPLE 5

To determine whether an increase in AGE-like immunoreactivity could be measured after a defined exposure to tobacco smoke, blood samples were obtained from a subject who habitually smoked, first after an 18-hour hiatus in smoking behavior, and then after the subject smoked five cigarettes consecutively at the end of the 18-hour hiatus. The degree of AGE modification of apoB was then compared in LDL fractions from these blood samples, using a standardized sandwich-type ELISA procedure to detect AGE-apoB. In performing this standardized assay, an anti-AGE antibody is immobilized on the surface of the assay wells to capture AGE-modified components of the sample, and a commercially available anti-apoB monoclonal antibody/horseradish peroxidase (HRP) conjugate is used to detect any AGE-modified apoB so immobilized by specific binding interaction with the immobilized anti-AGE antibodies.

Briefly, a low-density lipoprotein (LDL)-enriched serum fraction was prepared by treating a 100 $\mu$l serum sample with 900 $\mu$l 6.66% polyethylene glycol, m.w. 8000, for 15 minutes, centrifuging (14,000 rpm, 10 minutes), and solubilizing the resulting pellet in 100 $\mu$l 0.5% SDS overnight. To construct assay plates, an anti-AGE antibody, in this case the monoclonal antibody 4G9, is immobilized onto the surface of a micro titer plate by incubation at a titrated dilution, after which non-specific binding is blocked by replacing the capture antibody solution with a 1% solution of BSA. LDL-enriched serum fractions (or appropriately titrated dilutions of LDL standard) are then incubated in triplicate in the assay plates in a final concentration of 0.05% SDS in buffer and incubated for one hour, at which time the plates are rinsed and a titrated dilution of commercially available anti-apoB monoclonal antibody/enzyme conjugate (in this case anti-apoB/horseradish peroxidase (HRP) conjugate purchased from Biodesign International and used at 1:500 dilution) is added to detect any bound apoB. After a one-hour incubation the plates are washed and a suitable chromogenic HRP substrate, such as o-phenyline diamine (OPD) is added and, after an appropriate incubation period, OD is read at 50 nm versus a 570 nm reference wavelength. In general accordance with principles well known in the art, optimal concentrations of various reagents (e.g., the coating antibody and the detector antibody) and the optimal pH, detergent concentrations, buffer compositions, incubation periods, and other particular features are varied one against the other in order to maximize the sample signal and minimize interfering non-specific background "noise" in this sandwich-type immunometric assay for AGE-modification of apoB.

The pre-smoking AGE-apoB value in this experiment was 218±1 and the post-smoking value was 241±3 apoB-AGE Units per mg apoB (where one apoB-AGE Unit is defined as the activity of 1 $\mu$g/ml of a commercially available LDL standard (e.g., from Cappel). Applicants considered this evidence that smoking can acutely elevate AGE modification of a specific blood component, apoB of LDL. This suggests that measurement of AGE levels on sample components can provide information about the recent smoking history of a subject. Moreover, since AGE modification of LDL has been linked to pathogenic mechanisms that adversely affect human health, this further suggested to Applicants that smokers might benefit from interventions to limit excess AGE exposure that occurs as a result of tobacco consumption.

EXAMPLE 6

To discover whether AGE levels in a readily sampled tissue or fluid compartment reflect smoking history, Applicants examined serum samples obtained from consecutive patients presenting for pre-surgical screening at the North Shore University Hospital, Manhasset, N.Y. Some of these patients, by chance, were smokers (Group 1), others were non-smokers (Group 2). In this survey, the patient populations were not stratified or otherwise controlled for intensity of smoking, sex, age, health, or other characteristics that might have accounted for some of the variability in serum AGE levels. Serum AGE levels were determined by a competitive AGE ELISA method using a monoclonal anti-AGE antibody to detect AGEs relative to a standardized preparation of AGE-BSA (as detailed above in Example 1). Mean serum AGE levels were 200±80 for Group 1 (N=16) versus 150±30 for Group 2 (N=13). Comparison of this data set by t-test for independent means revealed that this difference was significant at the 0.05 probability level.

EXAMPLE 7

The AGEs of tobacco and tobacco products including, for example, tobacco smoke, also find utility as antigens or haptens, to elicit antibodies specifically directed to tobacco-related AGE structures. Such antibodies, likewise of the present invention, are useful in turn to identify and inhibit tobacco-related AGE structures. By constructing immunoassays employing anti-tobacco-related AGE antibodies of the present invention, for instance, the degree to which proteins are modified by tobacco-related AGEs can be measured. As discussed above, and depending on the half-life of the protein so modified, immunochemical measurement of AGE epitopes on a protein sample, such as serum proteins, provides an index of recent tobacco consumption e.g. by smoking. Likewise, immunochemical detection of AGE epitopes on circulating and/or tissue proteins can be used to monitor the course of treatment with agents of the present invention, which agents are directed toward inhibition of the excess accumulation of AGEs through tobacco use by reacting with AGEs in tobacco or tobacco smoke.

Various haptens, antigens, and conjugated immunogens corresponding to the tobacco-related AGEs of the present invention can conveniently be prepared, either by isolation of tobacco-related AGEs from tobacco or from tobacco smoke, for instance by making an AGE-containing aqueous extract of tobacco or of tobacco smoke condensate, as described above. This extract may then be used as an immunogen to raise a variety of antibodies which recognize specific epitopes or molecular features thereof. In a preferred embodiment, the AGEs of the extract are considered haptens, which are correspondingly coupled to any of several preferred carrier proteins, including for instance keyhole limpet hemocyanin (KLH), thyroglobulin, and most preferred, bovine serum albumin (BSA), using any of a number of well-known divalent coupling reagents such as a carbodiimide like EDC, according to protocols widely circulated in the art. Irrespective of the source, the tobacco-related AGEs whether alone or coupled to a carrier protein, and whether pure or in partially purified form, may be employed in any well-recognized immunization protocol to generate antibodies and related immunological reagents that are useful in a number of applications owing to the specificity of the antibodies for molecular features of the tobacco-related product.

Following a preferred protocol, any of several animal species may be immunized to produce polyclonal antisera directed against the tobacco-related AGE protein conjugate, including for instance mice, rats, hamsters, goats, rabbits, and chickens. The first of three of the aforesaid animal species are particularly desired choices for the subsequent production of hybridomas secreting hapten-specific monoclonal antibodies. The production of said hybridomas from spleen cells of immunized animals may conveniently be accomplished by any of several protocols popularly practiced in the art, and which describe conditions suitable for immortalization of immunized spleen cells by fusion with an appropriate cell line, e.g. a myeloma cell line. Said protocols for producing hybridomas also provide methods for selecting and cloning immune splenocyte/myeloma cell hybridomas and for identifying hybridomas clones that stably secrete antibodies directed against the desired epitope(s). Animal species such as rabbit and goat are more commonly employed for the generation of polyclonal antisera, but regardless of whether polyclonal antisera or monoclonal antibodies are desired ultimately, the hapten-modified carrier protein typically is initially administered in conjunction with an adjuvant such as Complete Freund's Adjuvant. Immunizations may be administered by any of several routes, typically intraperitoneal, intramuscular or intradermal; certain routes are preferred in the art according to the species to be immunized and the type of antibody ultimately to be produced. Subsequently, booster immunizations are generally administered in conjunction with an adjuvant such as alum or Incomplete Freund's Adjuvant. Booster immunizations are administered at intervals after the initial immunization; generally one month is a suitable interval, with blood samples taken between one and two weeks after each booster immunization. Alternatively, a variety of so-called hyperimmunization schedules, which generally feature booster immunizations spaced closer together in time, are sometimes employed in an effort to produce anti-hapten antibodies preferentially over anti-carrier protein antibodies.

The antibody titers in post-boost blood samples can be compared for hapten-specific immune titer in any of several convenient formats including, for instance, Ouchterlony diffusion gels and direct ELISA protocols. In a typical direct ELISA, a defined antigen is immobilized onto the assay well surface, typically in a 96-well or microtiter plate format, followed by a series of incubations separated by rinses of the assay well surface to remove unbound binding partners. By way of non-limiting example, the wells of an assay plate may receive a dilute, buffered aqueous solution of the hapten/carrier conjugate, preferably wherein the carrier protein differs from that used to immunize the antibody-producing animal to be tested; e.g. serum from tobacco-related AGE/KLH conjugate-immunized animal might be tested against assays wells decorated with immobilized tobacco-related AGE/BSA conjugate. Alternatively, the assay surface may be decorated by incubation with the hapten alone. Generally, the surface of the assay wells is then exposed to a solution of an irrelevant protein, such as casein, to block unoccupied sites on the plastic surfaces. After rinsing with a neutral buffered solution that typically contains salts and a detergent to minimize non-specific interactions, the well is then contacted with one of a serial dilution series of anti-serum prepared from the blood sample of interest (the primary antiserum). After rinsing again, the extent of test antibodies immobilized onto the assay wells by interaction with the desired hapten or hapten/carrier conjugate can be estimated by incubation with a commercially available enzyme-antibody conjugate, wherein the antibody portion of this secondary conjugate is directed against the species used to produce the primary antiserum; e.g. if the primary antiserum was raised in rabbits, a commercial preparation of anti-rabbit antibodies raised in goat and conjugated to one of several enzymes, such as horseradish peroxidase, can be used as the secondary antibody. Following procedures specified by the manufacturer, the amount of this secondary antibody can then be estimated quantitatively by the activity of the associated conjugate enzyme in a calorimetric assay. Many related ELISA or radioimmunometric protocols, such as competitive ELISAs or sandwich ELISAs, all of which are well known in the art, may optionally be substituted, to identify the desired antisera of high titer; that is, the particular antisera which give a true positive result at high dilution (e.g. greater than 1/1000 and more preferably greater than 1/10,000).

Similar immunometric protocols can be used to estimate the titer of antibodies in culture supernatants from hybridomas prepared from spleen cells of immunized animals. In so characterizing antisera or hybridoma supernatants, it is desirable to employ a variety of control incubations, e.g. with different carrier proteins, related but structurally distinct haptens or antigens, and omitting various reagents in the immunometric procedure in order to minimize non-specific signals in the assay and to identify reliable determinations of antibody specificity and titer from false positive and false negative results. The types of control incubations to use in this regard are well known. Also, the same general immunometric protocols subsequently may be employed with the antisera identified by the above procedures (i.e., antibodies found to be of high titer and to be directed against specific structural determinants of tobacco-related AGEs). Such latter applications of the desired anti-tobacco-related AGE antibodies, whether polyclonal or monoclonal, together with instructions and optionally with other useful reagents and diluents, including, without limitation, a set of molecular standards of the tobacco-related AGES, may be provided in kit form for the convenience of the operator.

Anti-tobacco-related-AGE antibodies generated as described, and particularly such monoclonal antibodies, also find use in the identification, separation, enrichment and purification of tobacco-related AGE epitopes. This may be accomplished by techniques known in the art, for instance, by exposing preparations known to contain the epitope of interest to immobilized antibodies specific for said epitope, washing away unbound material, and then eluting the specifically bound material and analyzing its chemical structure to determine specific molecular forms of tobacco-related AGEs.

EXAMPLE 8

To further demonstrate the utility of the AGE-inhibiting and AGE-reversing agents of the present invention to prevent the discoloration of protein on a surface, such as that which occurs on the tooth surface or on the skin or mucosal surfaces of smokers, the following surface browning experiment is performed. As a substitute for skin, mucosa or the pellicle-covered tooth surface, unexposed and developed photographic paper is used to provide an immobilized protein (gelatin, i.e., collagen) surface on a convenient paper backing. Five mm circles are punched from such photographic sheets, and several of these disks are then immersed in solutions of tobacco extract or tobacco smoke condensate (prepared as described above) that has been suitably diluted in an appropriate aqueous buffer (as described above), with or without an AGE-inhibiting or AGE-reversing agent of the present invention. Such experimental incubations are maintained, generally in the dark at a controlled temperature between 20° C. and 60° C., for a suitable time period which may range from several hours to several weeks. At various times after the incubation has been initiated, disks are recovered, observed for brown color and photographed for record keeping. Attachment of reactive AGEs from tobacco or smoke extracts causes the protein surface to become colored with yellow and brown AGE pigments in a manner analogous to the staining of skin, a mucosal surface or the tooth pellicle of tobacco users. Prevention of the accumulation of AGEs, as evidenced by the prevention of accumulation of yellow/brown pigments with reference to control disks not incubated with the test agent, identifies AGE-inhibiting agents useful in the context of the present invention.

In an alternative assay for AGE-reversing activity, protein-covered disks are "pre-browned" by incubation with the diluted tobacco extract or tobacco smoke condensate extracts as described supra, and a candidate AGE-reversing agent of the present invention is added to the incubation solution for a further period of time. Inhibition or reversal of the accumulation of yellow/brown pigments by test agents of the present invention, by reference to control disks not incubated with the test agent, identifies candidates particularly suitable for use as AGE-reversing agents in the context of the present invention. AGE-inhibiting and AGE-reversing agents so identified are particularly suitable for formulation as an oral rinses or as a dentifrice to prevent or reverse undesirable tooth staining and pigmentation of other oral surfaces that occurs in conjunction with tobacco use, whether orally as with chewing tobacco and snuff, or by smoking as with cigarettes, cigars and pipe tobacco. Test agents with activity in this protein-browning assay may also be formulated into creams, emollients or the like for use on the stained hands and fingers of tobacco smokers. This method also exemplifies a method of dosimetry useful in monitoring environmental smoke exposure.

EXAMPLE 9

Although cigarette smoking is widely accepted as a risk factor for cardiac, pulmonary, vascular, neoplastic and other diseases, the molecular mechanisms underlying this causal connection remain incompletely known. Both chronic and acute processes have been suggested to underlie pathogenic responses to tobacco use, but Applicants are the first to establish that tobacco consumption, particularly by smoking, can lead to elevated AGE levels in blood and tissues. Noting in their experiments that immunochemical staining with anti-AGE antibodies reveals that the coronary arteries of smokers with vascular diseases are heavily decorated with AGEs, Applicants also sought to confirm that chronic smoke exposure in vivo can lead to elevations in blood and tissue AGEs in a well-controlled animal model.

Using whole-body inhalation exposure chambers, six-week-old male and female rats (e.g., laboratory strain F344) are exposed, for various lengths of time ranging from a few weeks to 2 years, to an atmosphere of filtered air that is charged with a fixed burden of cigarette smoke particulates by dilution of mainstream smoke. Exposure for six hours per day, five days per week, for instance, to such an atmosphere carrying tobacco smoke at a level of 250 mg total particulate material (TPM) per cubic meter results in tobacco smoke deposits equivalent to those in the airways of humans smoking five packs of cigarettes per day. As described more fully in published procedures (e.g., J. Chen et al., 1989, *Inhalation Toxicol.* 1: 331–347), mainstream smoke is generated from type IR3 non-filter research cigarettes (Tobacco Health Research Institute; Lexington, Ky.) using continuous smoking machines. Control animals are identically housed but exposed to the filtered airstream only, without cigarette smoke. Smoke exposure levels are determined by reference to gravimetric analysis of filter samples taken from the exposure chambers. The chemical and physical characteristics of this smoke-exposure atmosphere have been described in detail (vide supra and J. Chen et al., 1992, *J. Aerosol Med.* 5: 19–30).

After the desired exposure period, test animals are sacrificed and various organs and tissues including, for instance, whole blood, are recovered and sampled for anatomical, microscopic, and biochemical analysis such as quantitation of AGE levels. In a preferred method, serum is diluted 1:5 in phosphate-buffered saline (PBS) and Proteinase K is added to $\frac{1}{100}$ the mass of total serum protein in the sample. Serum proteins then are digested by incubation at 37° C., and Proteinase K is inactivated by raising the temperature to 70° C. for 1 hour. After a brief centrifugation to clarify, the supernatants are collected and brought to 1 mM phenymethylsulfonyl fluoride (PMSF) before analysis for AGE content by AGE ELISA as described supra.

In preliminary studies conducted according to this procedure, serum protein digests from rats exposed to cigarette smoke for periods ranging from 6–85 weeks showed pooled mean (±std. dev.) AGE levels of 22.0±4.9 AGE Units/ml serum (N=13), while control rats not exposed to cigarette smoke showed mean serum protein AGE levels of 13.5±2.9 AGE Units/ml serum (N=7). The above method also provides a convenient assay by which to estimate the activity of agents and filter devices of the present invention in inhibiting, preventing or reversing the accumulation of AGEs due to tobacco consumption, as either the tobacco itself, the primary or mainstream tobacco smoke, the smoke-laden atmosphere, or the smoke-exposed animals may be treated according to the present invention, and the tissues and blood of the test animals then examined to determine the degree to which AGE accumulation thereby has been diminished, prevented or reversed by comparison to untreated or unexposed control samples.

EXAMPLE 10

The following example demonstrates that the glycotoxin removal filter also improves the organoleptic potential of cigarettes, and in particular, removes the "bite" from the taste of cigarette tobacco smoke resulting in a "smoother smoke."

In order to assemble the cigarettes for this test the following items were placed into a standard hand-held cigarette rolling machine, a standard commercial filter (cut off from a Marlboro light cigarette), 500 mg of aminoguanidine or an equivalent amount of sodium chloride, and a 3 cm length of a commercial cigarette in its original paper. The items were then bundled together using a piece of rolling paper. Rerolled cigarettes with additional filter material were indistinguishable from each other by sight or touch.

In order to conduct the test the examiner assembled pairs containing one of each type of cigarette (i.e. aminoguanidine or salt) and marked one of the pair with a small yellow dot. The cigarettes were then placed in a #10 envelope along with a smaller sealed envelope that contained the code (i.e. which cigarette had the yellow dot). In half of the envelopes the cigarettes with the aminoguanidine filter-add-in were marked with a yellow dot and in the other half the cigarettes with the sodium chloride filter-add-in were marked with a yellow dot.

Ten test subjects (including heavy smokers and occasional smokers) were each individually given one of the envelopes described above and asked to state their impressions of both cigarettes. Subjects responses were recorded by the examiner who then opened the inner envelope to reveal the code.

All 10 subjects agreed that the both cigarettes "tasted like a cigarette." Eight of the ten subjects were able to distinguish a subtle difference between the two cigarettes and all felt that the cigarette containing the aminoguanidine filter-add-in provided smoke with less "bite" or were a "smoother smoke." One subject stated "It's smoother the way an old red wine is smoother than a young one". All eight subjects who were able to distinguish between the two cigarettes preferred the one with the aminoguanidine filter-add-in.

EXAMPLE 11

This example demonstrates that the glycotoxin (AGE) removal filter is able to prevent cigarette smoke from staining of protein-coated surfaces. In this example microtiter plates coated with collagen were used, but the findings applied to any protein-coated surface such as teeth, nails or skin.

Test cigarettes containing aminoguanidine or sodium chloride filter-add-ins were prepared described in Example 4 and smoked in the apparatus also described therein. Five mls of PBS were placed in a 25 ml glass erhlemeyer flask with a sidearm and 20 cigarettes with either of the two different types of filter add-ins were successively mounted in a 500 ul pipette tip that penetrated the hole in the stopper of the flask and burned. Approximately 20 mm Hg was applied to the sidearm of the flask to draw smoke into the flask and into contact with the PBS. After all 20 cigarettes were burned, 5 additional mls of fresh PBS were added and then 2 mls of the mixture was added to each of three wells in a 6-well plate. Each 6-well plate had three wells with PBS exposed to smoke from the cigarettes with the aminoguanidine filter-add-ins and three wells with PBS exposed to smoke from the cigarettes with the sodium chloride filter-add-ins. Plates were incubated for 48 hours at 37° C. in the dark. Wells were then washed 6 times with PBS containing 0.05% Tween-20 and the color in the bottoms of the wells was compared. The color remaining in the wells was the colored AGEs that formed as a result of the interaction of the glycotoxins and/or reactive AGEs and the collagen-coated wells. Wells incubated with PBS exposed to smoke from the cigarettes with the sodium chloride filter-add-ins appeared brown in color while the wells incubated with PBS exposed to smoke from the cigarettes with the aminoguanidine filter-add-ins were not colored.

EXAMPLE 12

Spraying tobacco with aminoguanidine eliminates glycotoxins

In this example, tobacco leaves are treated with aminoguanidine, an inhibitor of AGE formation, and it is observed that glycotoxins are unable to promote the formation of AGE molecules in vitro. Loose tobacco leaves equivalent to the amount in 5 cigarettes were sprayed with 5 mls. of a solution containing the following concentrations of aminoguanidine: 10 mg/ml, 1 mg/ml, 0.1 mg/ml. After spraying, leaves were wrapped in aluminum foil and incubated at 37° C. for 7 days. Leaves were then rolled into cigarettes and smoked in the water-pipe device of Examples 3 and 4, described supra. Glycotoxin content was then measured using the in vitro AGE formation assay also described supra. As presented in FIG. 9, a dose dependent reduction in glycotoxin content was observed.

DISCUSSION

The foregoing disclosure and examples demonstrate the relevance and role of the biology and chemistry of protein glycation that has been elucidated earlier, with respect to the organoleptic properties and pharmacokinetics of tobacco treatment and consumption. Accordingly, since many of the vascular complications associated with cigarette smoking are also seen in diabetic patients who have high circulating and tissue bound AGE levels, the possibility was investigated herein that cigarette smoking promotes AGE formation. More particularly, the data presented herein includes the most recent showing that demonstrates and illustrates the presence and activity of a group of agents that are defined herein as glycotoxins. Both aqueous extracts of tobacco and cigarette smoke contain glycotoxins, highly reactive reducing sugars or glycation intermediates that can rapidly induce AGE formation on proteins in vitro and in vivo and cause DNA mutations in vitro. Both of these activities can be removed from the samples by passing the smoke through a dry column of aminoguanidine, a potent and specific inhibitor of the formation of AGEs.

Glycotoxins from cigarette smoke have a number of unique characteristics which distinguish them from the previously studied reducing sugars, glucose and glucose-6-phosphate. Foremost is their extreme reactivity: In marked contrast to glucose or glucose-6-phosphate both of which have been reported to take days to weeks to induce measurable AGE formation, tobacco-derived glycotoxins can induce AGE formation in hours. While most reducing sugars, such as glucose, require transport to gain access to the cell cytoplasm, glycotoxins appear to readily cross cell membranes of bacterial cells. In addition, glycotoxins can be absorbed through the lungs from cigarette smoke and in turn react with serum proteins in healthy people. Although we have not determined the chemical structure(s) of glycotoxins, we can surmise that they have carbonyl groups and probably dicarbonyls since they are removed or quenched by aminoguanidine. Glycotoxins are probably a product of the rearrangement of products formed during the Maillard reaction which is initiated during the tobacco curing process. The instability of the glycotoxins during isolation implies that they and other Maillard products, which likely are responsible for the aroma and flavor of smoke, are constantly being formed and lost as the tobacco is cured and then as it ages.

The formation of AGEs in vivo by tobacco glycotoxins, may be in part responsible for the increased incidence of atherosclerosis in cigarette smokers. There is abundant in vitro and in vivo evidence that AGEs play a role in the pathogenesis of atherosclerosis: (1) AGEs have been shown to crosslink connective tissue collagen which serves to increase connective tissue rigidity. (2) Collagen-linked AGEs serve as reactive "foci" to covalently trap circulating serum proteins, such as lipoproteins. (3) Binding of an endothelial cell's AGE receptors will increase vascular permeability, decrease synthesis of the anti-coagulant thrombomodulin and increase synthesis of the procoagulant tissue factor. (4) Tissue bound AGEs can chemically quench cell-derived nitric oxide activity thereby inhibiting the nitric oxide-dependent vascular relaxation. (5) AGE modification of amine-containing phospholipids has been shown to initiate lipid oxidation. Oxidized LDL is not recognized by cellular LDL receptors, and is removed by macrophage scavenger receptors. Lipid-laden vascular wall macrophages are the characteristic foam cells commonly found in the fatty streaks and other lesions typical of early atherosclerosis. (6) Markedly elevated vascular tissue and circulating AGEs have been linked to the accelerated vasculopathy of end-stage diabetic renal disease. (7) Exogenous AGE-modified albumin injected intravascularly into normal young rats and rabbits causes vascular alterations similar to those seen in animals with age- and diabetes-related vascular disease. Animals injected with exogenous AGE albumin show increases in vascular wall permeability, increased mononuclear cell migratory activity in subendothelial and periarteriolar spaces and defective blood pressure response after challenge with acetylcholine and nitroglycerin. [Vlassara et al PNAS 89: 12043–12047, 1992]. It is reasonable to expect that the AGEs formed by the reaction of glycotoxins with serum and tissue proteins would have the same activities as the previously described AGEs.

Glycotoxins may also contribute to the increased incidence of cancer in cigarette smokers. In addition to reacting with amino groups on proteins and lipids, reducing sugars can also react with the amino groups of nucleic acids. In vitro the incubation of either DNA or single nucleotides with reducing sugars produced absorbance and fluorescence changes similar to those observed for the AGE compounds bound to proteins and lipids. The incubation of bacterial plasmid DNA or mammalian shuttle vector DNA incubated with glucose or glucose-6-phosphate displayed considerable increase in mutation rates. (Bucala et al, 1984, PNAS 1984, 81: 105–109; Bucala 1985, PNAS 82: 8439–8442; Lee A T and Cerami, A. 1987, PNAS 84: 8311–8314). Since the previously studied reducing sugars are unable to cross the bacterial cell membrane, they do not cause mutations in bacteria if they are simply added to the bacterial growth media. Glucose-6-phosphate, however, has been shown to induce mutations in the glycolytic mutants of E. coli (DF40 and DF2000) which accumulate glucose-6-phosphate in their cytoplasm. A common feature amongst the results of all these studies is that the majority of mutations caused by the reducing sugars were either insertions or deletions.

The most compelling evidence for the mutagenicity of reducing sugars in mammals comes from work done by Lee et al. (1994) FASEB Journal 8: 545–550, on the effect of a maternal hyperglycemic environment on developing embryos in mice. Embryonic cells, like the lens of the eye and red blood cells, do not require insulin for transport glucose across their membranes. Transgenic mouse embryos that contained integrated copies of the bacterial gene, lac, a well-characterized mutagenesis marker, were transplanted into the uteri of streptozotocin-induced diabetic and control surrogate mothers. The lad mutation frequency was significantly higher in the DNA from the embryos transplanted into the diabetic mothers than in those transplanted into control mice.

Mammals with diabetes do not have a demonstrable increase in any type of cancer even though they have elevated serum glucose levels. Glucose does not freely enter mammalian cells; it requires the presence of insulin to stimulate its transport. Therefore in adult mammals, the intracellular glucose concentration is independent of the serum glucose level. It is important to note, however, that glycotoxins are far more potent than glucose. Like glucose and glucose-6-phosphate they can cause insertion and/or deletion mutants in an aminoguanidine-dependent manner, but unlike these other reducing sugars, glycotoxins can readily cross cell membranes.

In summary, our findings argue that glycotoxins, found in cigarette smoke, are responsible in part for the increased rates of atherosclerotic vascular disease and cancer seen among cigarette smokers. During the process of smoking, high concentrations of glycotoxins are inhaled into the alveoli where they may be both absorbed into the blood stream and taken up into the lung parenchymal cells. Once in the blood stream glycotoxins may induce the formation of AGE moieties on both serum and vascular wall proteins and thereby accelerate the development of atherosclerosis. Glycotoxins may also react with nucleic acids in the nuclei of the lung parenchymal cells to induce mutations and possibly cancer.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A filter for trapping and removing advanced glycosylation endproducts (AGEs) or other AGE-precedent glycotoxins present in tobacco smoke passed therethrough comprising a porous material containing a quantity of an agent uniformly disposed therein for contact with said smoke, wherein said agent is capable of reacting with glycosylation products to counteract an effect selected from the group consisting of AGE formation, deleterious activity of said AGEs, and the combination thereof.

2. A system for filtering tobacco smoke to inhibit the formation and reduce the amount and activity of advanced glycosylation endproducts, said system comprising a filter in accordance with claim 1 used in conjunction with a source of said tobacco smoke.

3. The system of claim 2, wherein said source of tobacco smoke is a cigarette, and said system comprises a filter fixedly attached to said source and in axial alignment therewith.

4. The system of claim 2, wherein said source of tobacco smoke is a pipe, said pipe comprising a stem, a mouthpiece, and a bowl, and said system comprises a filter disposed in fluid registry with the stem of said pipe disposed between the mouthpiece and the bowl containing said tobacco.

* * * * *